United States Patent [19]

Cook

[11] Patent Number: 5,665,562
[45] Date of Patent: Sep. 9, 1997

[54] DEVICES AND METHODS FOR THE MEASUREMENT OF CELLULAR BIOCHEMICAL PROCESSES

[75] Inventor: Neil David Cook, Peterston-Super-Ely, United Kingdom

[73] Assignee: Amersham International plc, Buckinghamshire, England

[21] Appl. No.: 373,316

[22] PCT Filed: May 16, 1994

[86] PCT No.: PCT/GB94/01040

§ 371 Date: Jan. 17, 1995

§ 102(e) Date: Jan. 17, 1995

[87] PCT Pub. No.: WO94/26413

PCT Pub. Date: Nov. 24, 1994

[30] Foreign Application Priority Data

May 17, 1993 [EP] European Pat. Off. .............. 93303806

[51] Int. Cl.$^6$ .............................. C12Q 1/16; G01N 23/06
[52] U.S. Cl. ........................... 435/35; 422/71; 436/804
[58] Field of Search ........................ 435/35; 436/57, 436/531, 535, 537, 804, 805; 422/71

[56] References Cited

U.S. PATENT DOCUMENTS

| | | | |
|---|---|---|---|
| 4,000,252 | 12/1976 | Kosak | 424/1 |
| 4,382,074 | 5/1983 | Hart | 436/537 |
| 4,568,649 | 2/1986 | Bertoglio-Matte | 436/534 |
| 4,588,698 | 5/1986 | Gruner | 436/535 |

FOREIGN PATENT DOCUMENTS

| | | |
|---|---|---|
| 0106662A3 | 4/1984 | European Pat. Off. . |
| WO9003844 | 4/1990 | WIPO . |
| 9003844 | 4/1990 | WIPO . |

OTHER PUBLICATIONS

Frank JS, The Myocardial Cell Surface . . . Circulation Research 41(4) 1977 pp. 702–714.
Langer GA, Calcium Exchange in a Single . . . Circulation Research 24(5) 1969 pp. 589–597.
Database WPI, Week 9301, Derwent Publications Ltd., AN 93–005910 (1992) (abstract) of JP Patent.
J.S. Frank et al., *Circulation Research*, 41(4), pp. 702–714 (1977).
G.A. Langer et al., *Circulation Research*, 24(5), pp. 589–597 (1969).

*Primary Examiner*—Ralph J. Gitomer
*Attorney, Agent, or Firm*—Wenderoth, Lind & Ponack

[57] ABSTRACT

Apparatus and method for studying cellular processes comprise a vessel having a base including a layer comprising a scintillant substance and which is adapted for attachment and/or growth of cells. Cellular processes are examined by scintillation proximity assay using a reagent labelled with a radioisotope.

18 Claims, 7 Drawing Sheets

DEVICES AND METHODS FOR THE MEASUREMENT OF CELLULAR BIOCHEMICAL PROCESSES

FIELD OF THE INVENTION

The present invention relates to the study of cellular and biochemical processes in living cells or in components of cells. Specifically described are devices and methods for the study of cellular and biochemical processes, utilising the Scintillation Proximity principle.

BACKGROUND TO THE INVENTION

1. Studies of Cellular Processes in Living Cells

Mammalian cell culture is an essential tool for fundamental research in eukaryotic biology and it has contributed to advances in virology, somatic cell genetics, endocrinology, carcinogenesis, toxicology, pharmacology, immunology and developmental biology (McKeehah, W. I., In Vitro Cell Dev. Biol., 26, 9–23, (1990)). Classical cell culture technology is carried out in nutrient mixtures with cells usually cultured as a monolayer attached to a hydrophilic surface, commonly sterile treated polystyrene. Considerable progress has been made in developing cell culture systems for specific cell types, with the aim of reconstructing the cell and its environment into a defined unit for the study of responses and properties of cells in a dynamic context. However, experimentation on such culture systems using biological assays is often limited by the need to use invasive or disruptive processes that compromise the structural and functional integrity of the cells.

Certain types of investigations lend themselves particularly to studies with whole cells and inevitably require cell culture techniques as an essential step in the investigation. General areas of study include: p1 (i) intracellular activity, including the replication and transcription of nucleic acids, protein synthesis and lipid metabolism, (ii) intracellular flux, ie. movement of RNA from cell nuclei to the cytoplasm, translocation of human receptor complexes, fluctuations in lipid and protein metabolic pools, transport of ions and other small molecules across membranes, (iii) environmental influences, including nutrition, infection, virally or chemically induced transformation, drug action and metabolism, response to external stimuli and secretion of specialised products, and (iv) cell-cell interaction, including embryonic induction, cell population kinetics, cell-cell adhesion and motility.

A vast array of radiolabelled ligands which are available commercially, has played a major role in the development of methods currently used to study intracellular activity, metabolism and cell-ligand interactions in cell culture assay systems. Particular examples relating to the study of cellular processes are:

Thymidine Uptake

Studies involving the measurement of [$^3$H] thymidine uptake currently suffer from an absolute requirement for cell disruption and consequently are prone to artifactual effects (Adams, R. L. P., Cell Culture for Biochemists, p181–192; Saegusa, Y. et al, J.Cell Physiol., 142, 488–495 (1990)). In addition to providing an assessment of cellular proliferation and growth in living cells, thymidine uptake studies are also used to study the extent of DNA repair and/or damage occurring during culture, in the presence or absence of external agents (McKeehan, W. et al, In Vitro Cell Dev. Biol., 26, 9–23, (1990)). Current methods however, require cell disruption and do not readily lend themselves to temporal studies. Thymidine uptake has been used more recently, in tandem with other potential markers, in the field of programmed cell death, or apoptosis, where there is currently considerable pharmacological and clinical interest (Tritton, T. and Hickman, J., Cancer Cells Quarterly Rev., 2, 95–105, (1990)). However, few of the current methods are able to explore and quantify spatial and temporal events occurring during apoptosis (Lock, R. B. and Ross, W. E., Proc. Amer. Assoc. Cancer Res., 30, 621, (1989)). [$^3$H] Thymidine uptake studies are also used in cell cycle studies in order to monitor regulation of this essential process (Studzinski, G. P.,Cell Tissue Kinetics, 22, 405–424, (1989) ). However, there are currently no methods available for the direct measurement of thymidine uptake in living cells.

Receptor Binding/Kinetic Studies

Most of the methods used in this field require binding of a radiolabelled ligand, followed by quantification of receptor number and affinity in competition studies at a fixed time (Goldstein, J. L. and Brown, M. S., Methods in Enzymol., 98, 241–260, (1985); Zoon, K. C. et al, J. Pharmaceutical and Biochemical Analysis, 7, 147–154, (1989)). These methods often utilise membrane filter assays in vitro. The majority of methods require release of cells from a monolayer and often necessitate isolation of cell membranes. These systems are therefore not suitable for real time kinetic studies. Thus in the cytokine field, where specific ligand-receptor binding studies are of fundamental importance, it is not possible to monitor binding, uptake and internalisation of specific radiolabelled ligands, as a function of time in living cells (Rakowicz-Szulczynska, E. W., et al, J. Immunol. Methods, 116, 167–173, (1989)). Currently disruptive techniques are required to differentiate between these important processes. This is also the case for studies of receptor cycling, an important process during the receptor-mediated endocytosis of a variety of essential ligands (Anderson, R. G. W., et al, Cell, 10, 351–364, (1977)).

Lipid Metabolism

Studies on the regulation of lipid biosynthesis are usually limited by the disruptive experimental procedures required to determine the incorporation of radioactively labelled lipid substrates. Such experiments are generally performed under optimal conditions in vitro, that may not reflect the situation in vivo, due to an inability to measure variations, both temporally and spatially, in living cells (Vance, D. E. and Vance, J. E., Biochemistry of Lipids and Membranes, pp.116–120, (1989)). The Hep G2 human tumorigenic cell line is currently widely used to investigate lipid and lipoprotein metabolism. Pulse-chase studies are currently difficult to perform when using radiolabelled precursors such as oleic acid, as a function of time. This is because there is a requirement for disruption of the cell in order to differentiate localized areas of uptake. To date, the only metabolic studies that can be carried out with living cells have used fluorescently labelled lipids (Pownall, H. J., Chem. Physics of Lipids, 50, 191–212, (1989)). There are, however, inherent problems with such studies since the fluorophors used tend to be extremely bulky relative to the lipid. The physiological integrity of such labelled lipids is therefore questionable and they are known to be taken up in Hep G2 cells at different rates and incorporated differently within the cell, relative to unlabelled lipid (Pownall, H. J.). Similar problems are also encountered in studies related to protein uptake and metabolism as seen for example when pulse-chase studies using radiolabelled methionine and/or leucine are carried out (Freshney, R. I., Culture of Animal Cells: A Manual of Basic Technique, 2nd Edition, Alan R. Liss Inc. (1987), pages 227–236). Unless fluorescent probes are used, disruption of the cell is always necessary (Smith, L. C., et al, Methods in Enzymol., 129, 858–873, (1986)).

Cell Calcium

Calcium concentrations in the cytoplasm are carefully regulated by several mechanisms and the affinity for calcium and its rate of transport across the membrane, vary considerably from cell to cell. In early cellular studies, calcium sensitive fluorescent dyes were injected invasively, thus restricting their usefulness in kinetic measurements. The more recent use of dyes such as Fura-2 has alleviated this problem, although quantitative, time-dependent measurements of calcium are still difficult to carry out in culture (Cavaggioni, A., Bioscience Results, 9(4), 421, (1989)). Alternatively, [$^{45}$Ca] (Kuwata, J. H. and Langer, G. A., Molecular Cell Cardiology, 21, 1195–1208, (1989)) and Langer, G. A. et. al., Circulation Res., 24, 589–597, (1969)) and 42K (Frank, J. S. et. al., Circulation Res., 41, 702–714, (1977)) exchange has been measured in cardiac cells. Using sterile scintillant coated discs in a flow cell chamber, neonatal rat hearts were cultured and the time dependent uptake of [$^{45}$Ca] and [$^{42}$K] was monitored by pulse-chase methods. Although time dependent measurements in living cells are recorded in this study, there are several disadvantages with this system: (i) the system is only applicable to one sample at a time, (ii) large quantities of [$^{45}$Ca] are used for uptake studies, (iii) there is a high background/non-specific signal and (iv) discs are removed from the sterile culture medium and exposed to air before insertion into the flow cell. There is therefore no opportunity to perform additional measurements or to continue to culture the sample.

Consequently, there is still a requirement, not only in this case for calcium uptake measurement, but also in the processes described previously, for non-invasive, non-disruptive, real-time whole cell measurements in a format which is amenable to high sample throughput. The invention described here is intended to overcome the problems and limitations of the prior art methods and will greatly facilitate the above objectives.

2. Developments in Scintillation Counting Technology

Detection of receptor binding or cellular metabolic events utilising radiolabelled substrates is accomplished by scintillation counting, usually following extraction or separative procedures, which are generally laborious, time consuming and are not amenable to automation.

A means for overcoming such problems is described in U.S. Pat. No. 4,568,649 (Bertoglio-Matte). This covers an homogeneous assay procedure which produces quantifiable light energy at a level which is related to the amount of radioactively labelled reactant in the assay medium. The light energy is produced by a scintillant which is either incorporated, or forms part of, a support structure (beads or other solid surface which can be used in the assay process). The support structures are coated with a receptor or other capture molecule, and are therefore capable of specifically binding the radiolabelled ligand or reactant of interest. In a direct assay, a sample containing the reactant is mixed in aqueous solution containing scintillant support bodies to which a binding compound may be attached. The reactant is caused to bind with its corresponding binding compound, thereby placing the radiolabelled species in close proximity to the scintillant-containing support. The scintillant is activated causing emission of light, which can be detected conventionally using a scintillation counter. The amount of light produced is directly proportional to the amount of reactant bound to the surface of the support structures.

Ideally the isotope of the radiolabel should have a relatively low energy beta-emission, for example tritium, or iodine-125 auger electrons. Only that portion of the sample which binds to the binding molecule, and is therefore in close proximity to the scintillant will result in scintillation events that can be counted. Unbound reactant will be at too great a distance from the scintillant surface to produce scintillations, the beta-decay energy being dissipated in the liquid aqueous medium.

A considerable advantage of the scintillation proximity assay process is that it does not require separation of bound molecular species from free. Such a process will also minimise the need to handle potentially hazardous/radioactive substances, as well as being more convenient and amenable to automation.

In U.S. Pat. No. 4,568,649, capture molecules are attached to, and fluorescer is integrated into beads, for example polyacrylamide beads. The Scintillation Proximity Assay technique may also be performed with other types of support structure. European Patent Application No. 0378059 describes a support structure for scintillation proximity assays comprising a fibre mat which incorporates a fluorescer. In one format the fibre mat consists of solid scintillant forming a matrix. The scintillant can be a cerium loaded glass or may be based in rare earths such as yttrium silicate (with or without activators such as $Tb^{3+}$, $Eu^{3+}$, $Li^+$). The scintillant fibre may also be composed of a scintillant polymer such as polyvinyltoluene. As an alternative, an organic scintillant such as 2,5-diphenyloxazole (PPO) or anthracene may be coated onto a fibre mat which is made from non-scintillant material. The fibre mesh format presents a large surface area upon which binding reactions can occur.

PCT Application No. WO 90/03844 discloses a microtitre well plate intended for binding assays. There is no claimed application for living cell-based assays. The sample plate may be produced from a transparent scintillant-containing plastic by means of a vacuum thermoforming or injection moulding process. In principle the walls of the plate may be coated with binding compound for the purpose of carrying out in vitro binding assays using radiolabelled reactants. However no practical examples are given in the application. It is possible, for example, that one disadvantageous effect of using a plate made from clear plastic will be that light generated in one well of the plate may be detected in adjacent wells, a phenomenon known as "cross talk", thereby causing high assay backgrounds and spurious assay results. The plates are not described as being treated in any way to support cell culture or growth.

Burton, J. A. and Hoop, B. describe a method and apparatus for ligand detection (PCT Application No. WO 88/04429). Central to the process is a reaction chamber and sensor surface connected optically to a detector. In a typical format of the method, a sample containing the ligand to be measured is introduced into the chamber containing receptor molecules immobilised on the sensor surface, and radioactively labelled ligand molecules. As a result, a portion of the labelled ligand molecules is displaced from the surface causing a decrease in fluorescent events at the sensor surface. However, the apparatus described in this application is designed for continuous throughput competitive binding assays. There is no reference to, or applications in, the study of living cells.

In summary, none of the prior art methods published for SPA are amenable to the study of biochemical processes in living cells. In part, this is due to the fact that the current fibre and bead based technologies are not suitable for monolayer cell culture. The only scintillant plate format so far described is intended for in vitro radiolabelled binding assays, and furthermore has inherent potential disadvantages outlined above for the specific applications which are the subject of this invention.

Description of the Invention

This invention provides in one aspect apparatus for studying a cellular process, comprising a vessel having an axis, an open top, side walls and a base, wherein the base includes a region and there is provided in or on an interior surface of the region a layer comprising a scintillant substance and being adapted for the attachment and/or growth of cells.

In one embodiment, the layer comprising a scintillant substance constitutes a base plate integral with the base of the vessel. In another embodiment, the layer comprising a scintillant substance is a disc positioned on the base of the vessel.

The invention also provides in another aspect a multiwell plate, such as a microtitre plate, comprising an array of wells held in fixed relationship to one another, wherein each well is a vessel as defined.

The invention provides in another aspect a method of studying a cellular process, by the use of a vessel as defined and of detection means for observing scintillation of the scintillant material, which method comprises providing cells adhering to the layer in the presence of a fluid medium, introducing into the fluid medium a reagent labelled with a radioisotope emitting electrons with a mean range up to 2000 µm, preferably up to 200 µm, in aqueous media, under conditions to cause a portion of the labelled reagent to become associated with or released from the cells adhering to the layer, and using the detection means to observe scintillation caused by radioactive decay so as to study the cellular process.

The invention provides in another aspect a method of studying a cellular process, by the use of a vessel as defined, and of detection means for observing scintillation of the scintillant substance, which method comprises introducing into the vessel a fluid suspension of cells or other structures labelled with a radioisotope emitting electrons with a mean range of up to 2000 µm in aqueous media, under conditions to cause a portion of the labelled cells or other structures to become associated with the layer, and using the detection means to observe scintillation caused by radioactive decay so as to study the cellular process.

The apparatus and method can be used for the measurement of a variety of cellular biochemical processes in real time using non-invasive techniques, that is to say techniques which do not compromise the integrity or viability of the cells.

Preferably, the cellular process is selected from the group consisting of biosynthesis, degradation, transport, uptake, movement, adherence, binding, metabolism, infection, fusion, biochemical response, growth and death.

The scintillant base plate is preferably optically transparent, both to allow cells in culture to be viewed using an inverted phase contrast microscope, and to enable the material to transmit light at a given wavelength with maximum efficiency. In addition the base retains its optical properties even after exposure to incident beta radiation from radioisotopes as well as under stringent radiation conditions required for sterilisation of the plates.

The base plate can be composed of any transparent material containing scintillant, e.g. a scintillant glass based on lanthanide metal compounds. In the preferred format, the base plate is composed of any plastic material, where normally the monomer units which comprise the polymer include phenyl or naphthyl moieties, in order to absorb incident radiation energy from radionucleotides which are in close proximity with the surface. Preferably the plastic base plate is composed of polystyrene or polyvinyltoluene, into which is incorporated a scintillant substance. The scintillant substance can include aromatic hydrocarbons such as p-terphenyl, p-quaterphenyl and their derivatives, as well as derivatives of the oxazoles and 1,3,4-oxadiazoles, such as 2-(4-t-butylphenyl)-5-(4-biphenylyl)-1,3,4-oxadiazole and 2,5-diphenyloxazole. Also included in the polymeric composition may be a wavelength shifter such as 1,4-bis(5-pheny-2-oxazolyl)-benzene, 9,10-diphenylanthracene, 1,4-bis(2-methylstyryl)-benzene etc. The function of the wavelength shifter is to absorb the light emitted by the scintillant substance and re-emit longer wavelength light which is a better match to the photo-sensitive detectors used in scintillation counters. Other scintillant substances and polymer bodies containing them are described in EPA 556005. The nature of the scintillant substance is not material to the invention.

The scintillant substances can be incorporated into the plastic material of the base by a variety of methods. For example, the scintillators may be dissolved into the monomer mix prior to polymerisation, so that they are distributed evenly throughout the resultant polymer. Alternatively the scintillant substances may be dissolved in a solution of the polymer and the solvent removed to leave a homogeneous mixture.

The base plate or disc may be bonded to the main body of the well or array of wells, which itself may be composed of a plastic material consisting of polystyrene, polyvinyltoluene, etc. In the case of the multi-well array, the body of the plate may be made opaque, ie. non-transparent and internally reflective, in order to completely exclude transmission of light and hence minimise "cross-talk". This is accomplished by incorporating into the plastic at the polymerisation stage a white dye or pigment, for example, titanium dioxide. Bonding of the base plate to the main body of the device can be accomplished by any suitable bonding technique, for example heat welding, injection moulding or ultrasonic welding.

BRIEF DESCRIPTION OF THE DRAWINGS

Reference is directed to the accompanying drawings, in which.

Each of FIGS. 4 to 13 is a graph or chart of scintillation microtitre plate radioactive counts per minute (SMPCPM) against time or other variable.

Figure 1A:
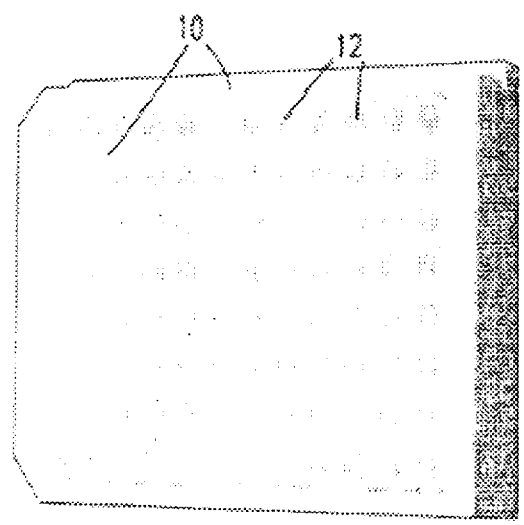
FIG. 1A and 1B are two-part perspective views of a multiwell plate according to the invention.
Figure 1B:
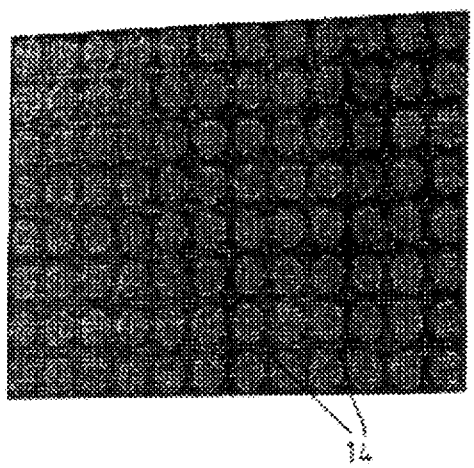

Referring to FIGS. 1A and 1B, a 96-well device is constructed to the standard dimensions of 96-well microtitre plates 12.8 cm×8.6 cm×1.45 cm with wells in an array of 8 rows of 12 wells each. The main body of the plate (Part A) is constructed by injection moulding of polystyrene containing a loading of white titanium oxide pigment at 12%. At this stage, the wells 12 of the microtitre plate 10 are cylindrical tubes with no closed end. A base plate (Part B) is formed by injection moulding of polystyrene containing 2-(4-t-butylphenyl)-5-(4-biphenylyl)-1,3,4-oxadiazole (2%) and 9,10-diphenylanthracene (0.5%). The base plate (Part B) has been silk screen printed with a grid array 14 to further reduce crosstalk. The base plate (Part B) is then fused in a separate operation to the body (Part A) by ultrasonic welding, such that the grid array 14 overlies the portions of the microtitre plate 10 between the wells 12.

Figures 2A, 2B:
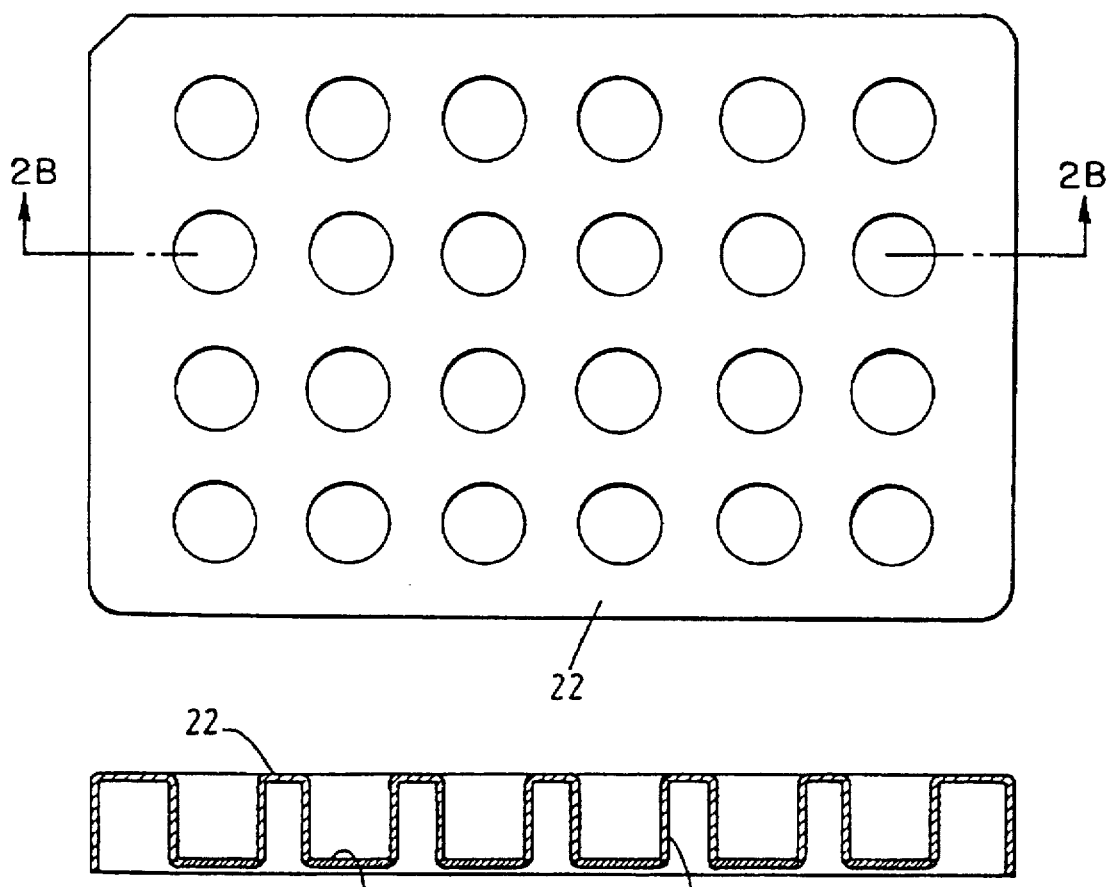
FIG. 2A and 2B is a two-part orthogonal view of another multiwell plate according to the invention.

Referring to FIGS. 2A and 2B, a 24-well device is constructed to the dimensions 12.8×8.6×1.4 cm with 24 wells in an array of 4 rows of 6 wells. The main body 22 of the plate (not including the base of each well) is constructed by injection moulding of polystyrene containing 12% white titanium oxide pigment. The base 24 of each well is injection moulded with polystyrene containing 2-(4-t-butylphenyl)-5-(4-biphenylyl)-1,3,4-oxadiazole (2%) and 9,10-diphenylanthracene (0.5%). The heat from the injected base plastic results in fusion to the main body giving an optically transparent base to the well.

When compared to the microtitre plate shown in FIG. 1, the design shown in FIG. 2 is fundamentally different in that the base of each well is discontinuous with the other wells in the array. In this embodiment the printed grid (used in FIGS. 1A and B) is not required to reduce inter-well crosstalk. Either construction may be used for 96-well, 24-well or other embodiments of the device.

Figure 3:
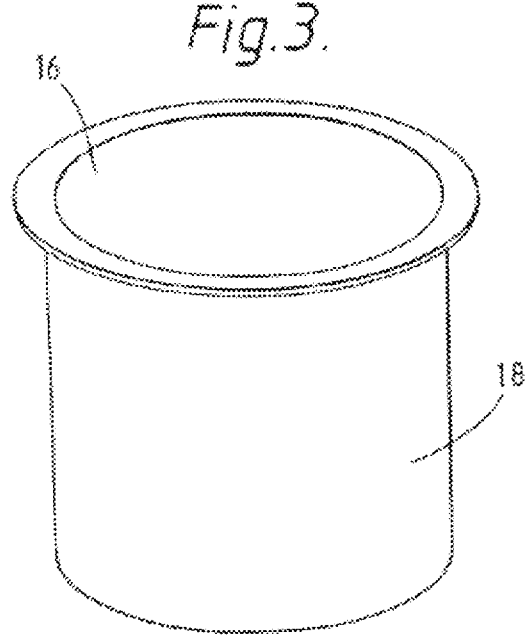
FIG. 3 is a perspective diagrammatic view of a single well device with a scintillant plastic base.
Figure 3:
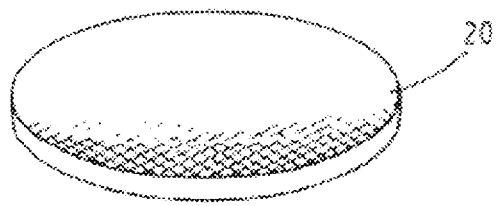

FIG. 3 shows a single vessel according to the invention having an open top 16, side walls 18 and an optically transparent scintillant plastic base 20 sealed round the lower edge of the side walls.

In this invention, the device can take various formats for the purpose of growing cells and studying cellular biochemical processes in living cells or cell fragments. In one format the device consists of a 96-well plate (shown in FIGS. 1A and B), which is a format typically used in experimental cell biology and one which is also suitable for use in a flat bed scintillation counter (e.g. Wallac Microbeta or Packard Top Count). In the multi-well format, it is an advantage to be able to prevent "cross talk" between different wells of the plate which may be used for monitoring different biological processes using different amounts or types of radioisotope. Therefore the main body of the plate is made from opaque plastic material.

As an alternative format (FIGS. 2A and B), the device may be in the form of a 24-well plate which is a more commonly used format for cell culture. This type of plate is also suitable for counting in a flat bed scintillation counter. The dimensions of the wells will be larger enabling more cells to be grown.

In another format (FIG. 3), the invention consists of a single well or tube. The tube may be constructed from a hollow cylinder made from optically transparent plastic material and a circular, scintillant containing, plastic disc. The two components are welded together so as to form a single well or tube suitable for growing cells in culture. As in the plate format, bonding of the circular base plate to the cylindrical portion is achieved by any conventional bonding technique, such as ultrasonic welding. The single well or tube may be any convenient size, suitable for scintillation counting. In use, the single well may either be counted as an insert in a scintillation vial, or alternatively as an insert in a multi-well plate of a flat bed scintillation counter. In this latter case, the main body of the multi-well plate would need to be opaque for reasons given earlier.

As an alternative non-preferred format, the transparent, scintillant containing plastic disc is made to be of suitable dimensions so as to fit into the bottom of a counting vessel. The counting vessel is made from non-scintillant containing material such as glass or plastic and should be sterile in order to allow cells to grow and the corresponding cellular metabolic processes to continue. Cells are first cultured on the disc, which is then transferred to the counting vessel for the purposes of monitoring cellular biochemical processes.

The culture of cells on the scintillation plastic base plate of the wells (or the disc) involves the use of standard cell culture procedures, e.g. cells are cultured in a sterile environment at 37° C. in an incubator containing a humidified 95% air/5% $CO_2$ atmosphere. Various cell culture media may be used including media containing undefined biological fluids such as foetal calf serum, or media which is fully defined and serum-free. For example, MCDB 153 is a selective medium for the culture of human keratinocytes (Tsao, M. C., Walthall, B. J. and Ham, R. G., J. Cell. Physiol., 110, 219–229, (1982)).

The invention is suitable for use with any adherent cell type that can be cultured on standard tissue culture plasticware. This includes the culture of primary cells and both normal and transformed cell-lines. These cells may be derived from all recognised sources with respect to (i) species, e.g. human, rodent, simian, (ii) tissue source, e.g. brain, liver, lung, heart, kidney, skin, muscle and (iii) cell type, e.g. epithelial, endothelial, mesenchymal, neuroectodermal. In addition, cells that have been transfected with recombinant genes may also be cultured using the invention. There are established protocols available for the culture of many of these diverse cell types (Freshney, R. I., Culture of Animal Cells: A Manual of Basic Technique, 2nd Edition, Alan R. Liss Inc. (1987)). These protocols may require the use of specialised coatings and selective media to enable cell growth and the expression of specialised cellular functions. However, none of these protocols are precluded from use in the invention.

The scintillating base plate or disc, like all plastic tissue culture ware, requires surface modification in order to be adapted for the attachment and/or growth of cells. Treatment preferably involves the use of high voltage plasma discharge, a well established method for creating a negatively charged plastic surface (Amstein, C. F. and Hartmann, P. A., J. Clinical Microbiol., 2,1, 46–54, (1975)). For many cell types, this surface is suitable for both growth and assay purposes. However, cell attachment, growth and the expression of specialised functions can be further improved by applying a range of additional coatings to the culture surface of the device. These can include: (i) positively or negatively charged chemical coatings such as poly-lysine or other biopolymers (McKeehan, W. L. and Ham, R. G., J. Cell Biol., 71, 727–734, (1976)); (ii) components of the extracellular matrix including collagen, laminin, fibronectin (Kleinman, H. K. et. al., Anal. Biochem., 166, 1–13, (1987)) and (iii) naturally secreted extracellular matrix laid down by cells cultured on the plastic surface (Freshney, R. I.). Furthermore, the scintillating base plate may be coated with agents such as lectins, or adhesion molecules to enable the attachment of cell membranes or cell types that normally grow in suspension. Methods for the coating of plasticware with such agents have been described previously, see for example, Boldt, D. T. and Lyons, R. D., J. Immunol., 123, 808, (1979)).

In addition, the surface of the scintillating layer may be coated with living or dead cells, cellular material, or other coatings of biological relevance. The interaction of radiolabelled living cells, or other structures with this layer can be monitored with time allowing processes such as binding, movement to or from or through the layer to be measured.

Virtually all types of biological molecules can be studied using this invention. That is, any molecule or complex of molecules that interact with the cell surface or that can be taken up, transported and metabolised by the cell, can be examined using real time analysis. Examples of biomolecules will include, receptor ligands, protein and lipid metabolite precursors, (e.g. amino acids, fatty acids), nucleosides and any molecule that can be radiolabelled. This would also include ions such as calcium, potassium, sodium and chloride, that are functionally important in cellular homeostasis, and which exist as radioactive isotopes. Furthermore, viruses and bacteria and other cell types, which can be radiolabelled as intact moieties, can be examined for their interaction with monolayer adherent cells grown in the scintillant well format.

The type of radioactive isotope that can be used with this system will typically include any of the group of isotopes which emit electrons having a mean range up to 2000 μm in aqueous media. These will include isotopes commonly used in biochemistry such as [$^3$H], [$^{125}$I], [$^{14}$C], [$^{35}$S], [$^{45}$Ca], [$^{33}$P] and [$^{32}$P], but does not preclude the use of other isotopes such as [$^{55}$Fe], [$^{109}$Cd] and [$^{51}$Cr] which also emit electrons within this range. The wide utility of the invention for isotopes of different emission energy is due to the fact that the current formats envisaged would allow changes to the thickness of the layer comprising a scintillant substance, thereby ensuring that all the electron energy is absorbed by the scintillant substance. Furthermore, cross-talk correction software is available which can be utilised with all high energy emitters.

The following Examples are summarised with reference to the categories i) to iv) listed above in the Background to the Invention.

| Example | Application | Category |
| --- | --- | --- |
| 1 | Protein Synthesis | i) |
| 2 | Ca$^{2+}$ transport | ii) |
| 3 | Receptor-Ligand binding | iii) |
| 4 | Cell adhesion | iii) and iv) |
| 5 | Sugar transport and metabolism | ii) and iii) |
| 6 | Hormonal stimulation of process | ii) and iii) |
| 7 | Growth factor regulation of process | ii) and iii) |
| 8 | Thymidine transport | ii) |
| 9 | Growth factor stimulated motility | iii) and iv) |
| 10 | Metal induction of protein synthesis | i), ii) and iii) |
| 11 | Range of isotopes of use | not applicable |

EXAMPLE 1

Measurement of Protein Biosynthesis by Incorporation of [$^3$H] Methionine into HaCaT Cells Introduction The measurement of amino acid uptake and incorporation into protein or other biomolecules has been widely used to study mammalian cell metabolism. In particular, such studies have helped characterise the metabolic changes occurring in many disease states including diabetes, renal failure, cirrhosis and cancer [Munro, H. N. (1993) In Amino acids: metabolism and medical applications (eds: G L Blackburn, J. P. Grant & V. E. Young) pp. 1–10, PSG Inc. USA].

The cellular uptake of amino acids is mediated by multiple independent transport systems distinguished by substrate preference and by ionic requirements [McGivan, J. D. & Pastor-Anglada (1994) Biochem. J., 299, 321–324]. The uptake process, which can be sodium dependent or independent, is often closely coupled to specific cellular metabolic pathways or physiological events. Thus, amino acid uptake can be a useful marker for studying these cellular events.

We have utilized the Scintillation Microtitre Plate to investigate the feasibility of non-invasive real time measurement of amino acid uptake and subsequent protein biosynthesis using the tritium labelled amino acid methionine and cultured epithelial cells.

Materials and Methods

Cell Culture

HaCaT cells (Boukamp, P. et. al., J. Cell. Biol., 106, 761–771 (1988)), a spontaneously immortalized human skin keratinocyte cell line, were cultured in Dulbecco's modification of Eagle's media with 3.7 g/l sodium bicarbonate (DMEM), 2 mM L-glutamine, 50 IU/ml penicillin, 50 μg/ml streptomycin (all from Flow Labs) and 10% foetal calf serum (Gibco) (total DMEM) at 37° C. in a humidified incubator with a 95% air/5% CO$_2$ atmosphere.

L-[methyl-$^3$H]methionine uptake

HaCaT cells were seeded at approximately 5×10$^4$ per well in total DMEM into the 96 well scintillation microtitre plates (described on page 9 of this application). The cells were cultured in these plates at 37° C. in humidified 95% air/5% CO$_2$ for 48 hours without any media change. Following this incubation the total DMEM media was removed and replaced with 100 μl/well DMEM without methionine (Flow Labs), supplemented with 2 mM L-glutamine, 50 IU/ml penicillin, 50 μg/ml streptomycin, 10% foetal calf serum and 50 μCi/ml L-[methyl-$^3$H]methionine (Amersham International, TRK 583, 82 Ci/mmol).

Negative control wells included the addition of 10 μl of 1 mg/ml cycloheximide (Sigma), a protein synthesis inhibitor, in phosphate buffered saline (PBS) either immediately following the addition of activity (T=0), or after 5 hours incubation in the presence of [$^3$H]methionine.

The scintillation microtitre plates were incubated under conditions as described above for the following 28 hours and the uptake of [$^3$H]methionine was monitored by the direct counting of the plates at regular intervals in the Wallac Microbeta scintillation counter.

Results

Figure 4:
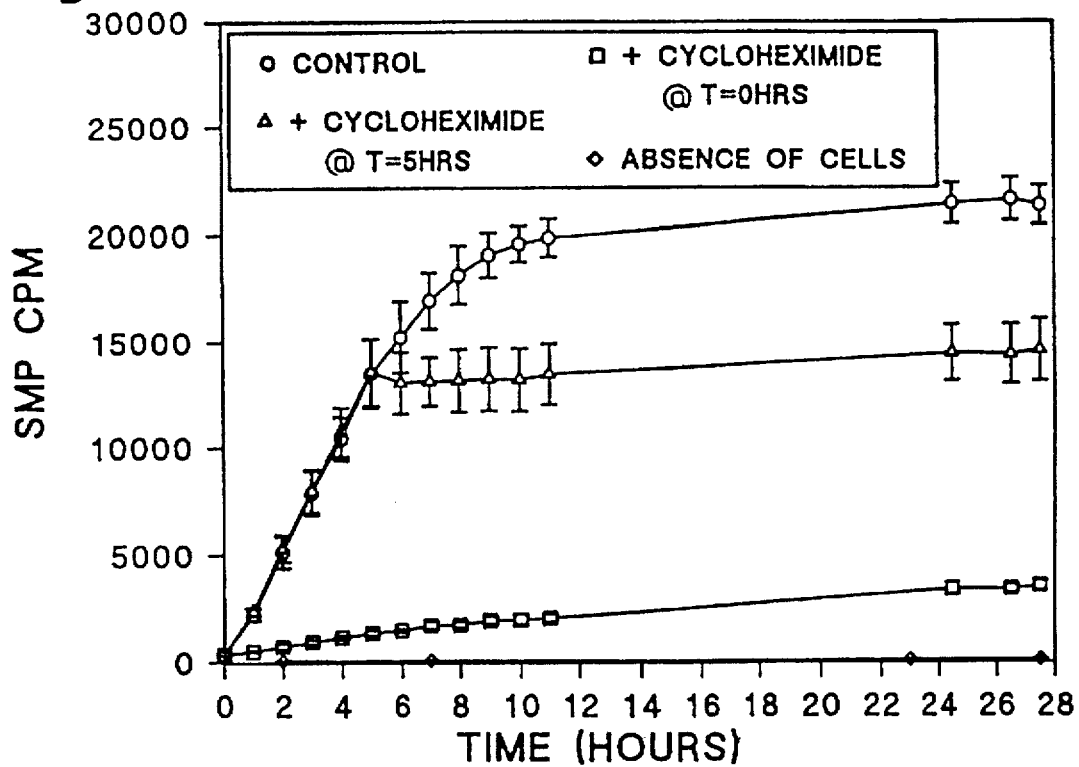

The timecourse for the uptake of [$^3$H]methionine monitored by direct counting in the Wallac Microbeta scintillation counter is shown in FIG. 4. Open circles show the mean (n=6) timecourse for the uptake of [$^3$H]methionine in the absence of any protein synthesis inhibitors. The remaining two data sets in FIG. 4 show the extent of inhibition of [$^3$H]methionine uptake in the presence of cycloheximide added either immediately after the addition of activity (T=0, open squares n=6), or after 5 hours (open triangles n=4).

A linear increase in the signal was obtained over the first 5 hours of the experiment in the absence of inhibitor. The addition of cycloheximide (0.1 mg/ml) at either T=0 hours or T=5 hours inhibited the rate of accumulation of activity indicating that this effect was due to cellular protein synthesis (Obrig, T. G. et. al., J. Biol. Chem., 264, 174 (1971)).

The presence of the inhibitor from T=0 caused 80% inhibition of [$^3$H]methionine uptake into the cells after 24–27 hours incubation. The addition of the cycloheximide at 5 hours caused an immediate halt in the uptake of radiolabelled methionine which was maintained for the duration of the experiment.

Examination of the cultured cells in the scintillation microtitre plates under the light microscope confirmed that the cells in both test and negative control wells remained adhered to the base of the wells throughout the experiment. This confirms that the reduced signal detected in the presence of cycloheximide was due to the inhibitory action of this substance on protein synthesis rather than by the loss of dead cells from the base of the well.

Conclusion

The results show that incorporation of [$^3$H]methionine into cells cultured on the scintillation microtitre plate described in this invention can easily be measured in real time by repeated direct counting of the plate in a flat bed scintillation counter. The quantitation procedure is non-invasive and does not compromise the structural and functional integrity of the cells. This example, therefore, demonstrates the great potential of the invention to perform temporal studies of cellular biochemical processes.

EXAMPLE 2

Measurement of [$^{45}$Ca] Transport into HaCaT Cells

Introduction

The influx of calcium ions into cells is one of the fundamental mechanisms of cell activation. Historically, $Ca^{++}$ influx has focused on voltage gated and receptor operated $Ca^{++}$ channels present on the membranes of excitable cells. Recently, however, it has become clear that most if not all cells have additional influxes that are concerned with intracellular homeostasis rather than cellular excitation. [Meldolesi, J., Current Biology, 3/12, 910–912 (1993)]. Various receptor mediated signal transduction pathways result in mobilization of calcium from intracellular stores. The depletion of these stores initiates uptake of extracellular $Ca^{++}$ to enable the cell to replenish the intracellular stores via a $Ca^{++}$ ATPase present in the membranes of the endoplasmic reticulum. [Putney, J. W. and Bird G. St. J., Cell, 75, 199–201 (1993)]. Agents such as thapsigargin, which inhibit $Ca^{++}$ ATPases cause depletion of intracellular stores and thus mimic the ability of agonists of the signal transduction pathways to activate $Ca^{++}$ uptake across the plasma membrane. [Thastrup et al, Proc. Natl. Acad. Sci. USA, 87, 2466–2470 (1990)].

We have utilized the Scintillation Microtitre Plate to show that thapsigargin-induced calcium uptake into cells can be measured conveniently in real time and without disruption of the cells.

Materials and Methods

Cell Culture

HaCaT cells [Boukamp, P. et al, J. Cell. Biol., 106, 761–771 (1988)], a spontaneously immortalized human skin keratinocyte cell line, were cultured in Dulbecco's modification of Eagle's media with 3.7 g/l sodium bicarbonate (DMEM), 2 mM L-glutamine, 50 IU/ml penicillin, 50 µg/ml streptomycin (all from Flow Labs) and 10% foetal calf serum (Gibco) at 37° C. in a humidified incubator with a 95% air/5% $CO_2$ atmosphere.

[$^{45}$Ca] uptake

HaCaT cells were seeded at approximately 1×10$^5$ cells per well in DMEM into a 96-well scintillation microtitre plate. The cells were cultured at 37° C. in a humidified atmosphere of 5% $CO_2$ in air for 48 hours with a media change after 24 hours. Following incubation, the DMEM was removed and replaced with 100 µl DMEM containing 2µCi/ml [$^{45}$Ca]-calcium chloride (Amersham; CES 3) with or without 50 nM thapsigargin (Calbiochem 586005).

The Scintillation Microtitre Plates were incubated under the conditions described above for 9 hours and the uptake of [$^{45}$Ca] monitored by direct counting of the plates at regular intervals in the Packard TopCount scintillation counter.

After 4 hours, the [$^{45}$Ca] containing medium was removed from half the wells and replaced with [$^{45}$Ca]-free DMEM with or without 50 nM thapsigargin where appropriate, and counting was resumed until the end of the timecourse.

Results

Figure 5:
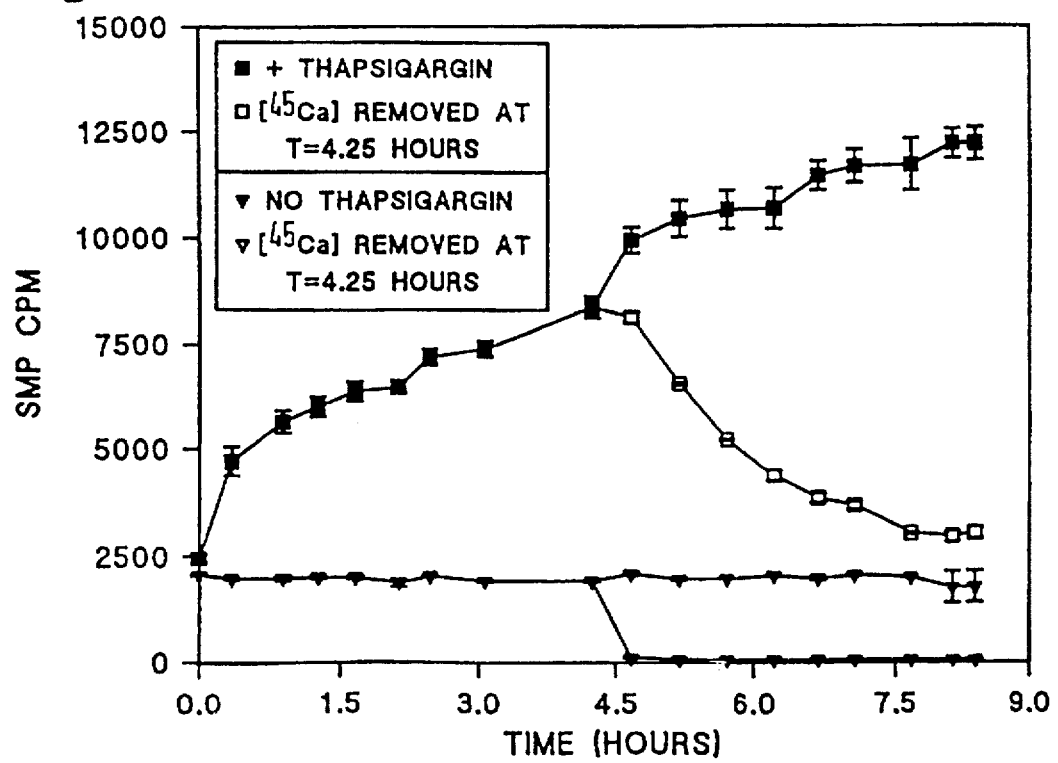

The timecourse for the uptake of [$^{45}$Ca] into HaCaT cells monitored by direct counting in a Packard TopCount scintillation counter is shown in FIG. 5. Solid squares show the mean (±SEM) timecourse for uptake of [$^{45}$Ca] in the presence of thapsigargin. Solid inverted triangles show the uptake of [$^{45}$Ca] in the absence of thapsigargin. Open symbols show the activity levels detected following the removal of [$^{45}$Ca] from the wells after 4.25 hours incubation.

The data shows a rapid initial phase of uptake followed by a slower prolonged phase over the remainder of the timecourse in the presence of thapsigargin. The removal of [$^{45}$Ca] from the medium results in a time dependent efflux of accumulated [$^{45}$Ca] from within the cell indicating a reversible transport process.

In the absence of thapsigargin, no detectable [$^{45}$Ca] entry is apparent throughout the time course. The level of activity detected is equivalent to the non proximity counts of the [$^{45}$Ca] in solution without cells on the scintillating base plate. If [$^{45}$Ca] is removed from the medium in the absence of thapsigargin, activity is immediately reduced to background levels confirming that no detectable uptake of [$^{45}$Ca] has occurred.

Examination of the cultured cells using light microscopy confirmed that cells remained adhered to the base of the wells and appeared to be in good condition.

Conclusion

The results show that the Scintillation Microtitre Plate described in this invention can be conveniently used to detect the uptake and efflux of calcium ions into living cells using [$^{45}$Ca]. The measurement, by repeated direct counting of the plate in a flat bed counter, is non invasive, requires no separation step, and minimises the handling and quantity of isotope used. This example, therefore, demonstrates the versatility of the invention enabling the study of transport processes involving small ions.

EXAMPLE 3

Measurement of [$^{125}$I]Epidermal Growth Factor Binding to Receptors on A431 Cells Introduction The binding of a ligand to a receptor often represents the first step in a complex cascade of biochemical events associated with a signal transduction pathway. Consequently the receptor provides an attractive accessible target for intervention by therapeutic agents.

Receptor binding assays have been extensively used to characterise and classify receptors and to identify receptor agonists and antagonists as potential drugs. Classically these assays have utilized radiolabelled ligands and membrane preparations derived by disruption of cells or tissues containing the receptor of interest. [Cuatrecasas P. and Hollenberg M (1976), Adv. Protein Chem., 30, 252]. As this approach generally results in loss of cellular integrity, certain aspects of the regulation of receptor expression such as receptor turnover and coupling to the effector pathway, cannot be studied. Furthermore, cells which normally grow in a well defined orientation often lose phenotypic characteristics when dissociated.

The Scintillation Microtitre Plate enables the study of cell cultures which normally grow as an adherent monolayer on culture treated plastic or on a layer of extracellular matrix proteins. This system is therefore potentially suitable for carrying out ligand binding assays in an homogeneous format without disturbing the equilibrium between bound and free ligand, and whilst maintaining the cells in a more physiological environment. In this example we have examined the real time association and dissociation of iodinated Epidermal Growth Factor with specific receptors expressed on A431 human carcinoma cells.

Materials and Methods

Cell Culture

A431 cells, a human epidermoid carcinoma cell line expressing Epidermal Growth Factor (EGF) receptors, were cultured in Dulbecco's modification of Eagles media (DMEM) with 2 mM L-glutamine, 50 IU/ml penicillin, 50 µg/ml streptomycin (all from ICN/#Flow) and 10% (v/v) foetal calf serum (Advanced Protein Products Ltd) at 37° C. in a humidified incubator with a 95% air/5% $CO_2$ atmosphere.

Receptor Binding

A431 cells were seeded at approximately $1 \times 10^5$ cells per well in DMEM into a 24-well Scintillation Microtitre Plate. The cells were cultured at 37° C. in a humidified atmosphere of 5% $CO_2$ in air for 48 hours or until confluent. Following incubation the DMEM was removed and replaced with 200 µl assay buffer (20 mM Hepes, 0.1% Bovine serum albumin (BSA), pH7.5) containing [$^{125}$I]EGF (Amersham IM196) at a concentration of approximately 500 pM (equivalent to 76,000 gamma counts per well). Non specific binding (NSB) was determined in the presence of 100 nM cold EGF (Sigma E.3264). At equilibrium, the dissociation of bound [$^{125}$I] EGF was initiated by the addition of unlabelled EGF (100 nM) in a minimal (5 µl) volume of assay buffer.

The Scintillation Microtitre Plates were monitored continuously at room temperature for binding of [$^{125}$I]EGF ligand to A431 EGF receptors by direct counting in the Wallac Microbeta scintillation counter.

Results

Figure 6:
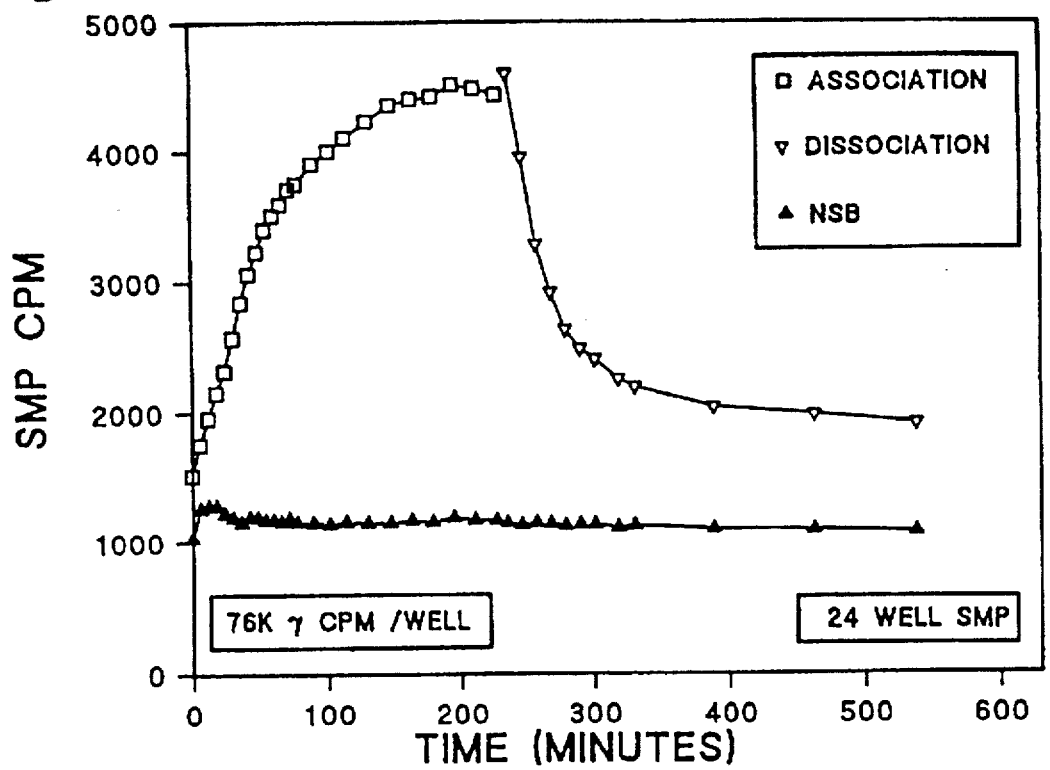

The association and dissociation time courses for [$^{125}$I] EGF binding to A431 cells are shown in FIG. 6. Open squares show the association of 500 pM [$^{125}$I]EGF. Open inverted triangles show the dissociation of [$^{125}$I]EGF induced by addition of unlabelled EGF (100 nM) at equilibrium. Solid triangles show the non specific binding of labelled EGF to the cells as determined by binding in the presence of excess unlabelled EGF (100 nM).

The data shows that the time course for EGF association to the EGF receptor is typical for a ligand binding interaction, with equilibrium of bound and free ligand apparent after approximately 200 minutes incubation at room temperature. Initiation of dissociation by addition of excess unlabelled EGF results in a rapid dissociation of labelled EGF from the receptors on the surface of the cells. The initial rapid phase of dissociation is followed by a much slower dissociation rate, consistent with 2 or more affinity states of the receptor. EGF receptors have been shown to express high and low affinity receptors in many studies, especially in assays using adherent cell monolayers. [Carpenter, G. and Cohen, S., (1990), J. Biol. Chem., 265, 7709–7712]. In this system non-specific binding remains constant throughout the time course.

Conclusion

The results show that the Scintillation Microtitre Plate can be used to quantify real time ligand binding to adherent cell monolayers. This should greatly facilitate the determination of kinetic parameters such as on and off rates without disturbing the binding equilibrium and where receptor expression is regulated in a physiological manner. The use of the 24 well plate version of the Scintillation Microtitre plate enables a larger and more accurate signal to be determined due to its 4.75 fold greater surface area compared to the 96 well plate.

EXAMPLE 4

Measurement of Magnesium Ion Induced Adhesion of [$^{14}$C]Labelled Ramos Cells to Immobilized Fibronectin Introduction Cell adhesion molecules are diverse cell surface glycoproteins that mediate cell to cell and cell to matrix adhesion. The process of cell adhesion is central to the recruitment of circulating white blood cells such as leucocytes and lymphocytes to the sites of inflammation and tissue injury. [Springer, T. A. (1994), Cell, 76, 301–314]. In addition, adhesion molecules are important factors in determining the malignant and metastatic potential of tumour cells. [Rougon, G, et al, (1992), The Cancer Journal, 5, 137–141].

The integrins are a group of non covalently linked heterodimeric adhesion molecules which are key components of many adhesion processes. Each member of the family is composed of a single $\alpha$ subunit and a single $\beta$ subunit of which 14 and 8 different variants respectively have been identified [Hynes, R. O., (1992), Cell, 69, 11–25]. Integrin expression is a highly regulated process with transient upregulation of integrin activity mediated by the binding of cations to extracellular binding sites and/or by conformational changes induced by cytoplasmic factors including the cytoskeleton [Haimovich, B, et al (1993), J. Biol. Chem., 268/21, 15,868–15,877].

The integrin $\alpha 4\beta_1$ or VLA4, expressed on lymphocytes and a number of cell lines, is a counter-ligand for vascular cell adhesion molecule (VCAM) and for the extracellular matrix protein Fibronectin [Chan, P-Y and Aruffo, A (1993), J. Biol. Chem., 268/33, 24,655–24,664]. We have used the Scintillation Microtitre Plate to quantify the magnesium ion induced adhesion of Ramos cells expressing the integrin VLA4 to immobilized cellular fibronectin.

Materials and Methods

Coating of Scintillation Microtitre Plate with Cellular Fibronectin

Cellular fibronectin (Sigma) was diluted to 3 µg/ml in 20 mM Tris-HCl pH8.5 and 300 ng of fibronectin added to the wells of an untreated 96 well scintillation microtitre plate (non sterile, non tissue culture treated). The plate was incubated at room temperature overnight. Negative control wells containing no fibronectin were included on each plate (20 nM Tris-HCl pH8.5). Following overnight incubation, unbound fibronectin was removed and the plate washed with magnesium/calcium free-phosphate buffered saline (PBS). Non-specific adhesion sites were then blocked by treatment of the plate with 1% dried milk in PBS. The plates were incubated at room temperature for 90 minutes. Excess blocking reagent was removed and the plate washed with magnesium/calcium free PBS before use.

Cell Culture

Ramos cells (ATCC:CRL 1596), derived from an American Burkitts Lymphoma, were maintained in RPM1 1640 containing 2 mM L-Glutamine, 50 IU/ml penicillin, 50 µg/ml streptomycin (all FLOW Labs.) and 10% foetal calf serum (GIBCO) at 37° C. in a humidified incubator with a 95% air/5% $CO_2$ atmosphere.

L-[methyl-$^{14}$C]methionine Labelling of Ramos Cell Line

Ramos cells were resuspended at a concentration of $1.5 \times 10^5$ cells/ml in RPMI 1640 depleted of methionine but supplemented with 2 mM L-Glutamine, 50 IU/ml penicillin, 50 µg/ml streptomycin, 10% foetal-calf serum and 4 µCi/ml L-[methyl-$^{14}$C]methionine (Amersham International, CFA 152, 55 mCi/mmol). The cells were cultured overnight at 37° C. in a humidified incubator with a 95% air/5% $CO_2$ atmosphere.

Cell Adhesion Assay

Before use in the adhesion assay the Ramos cells were harvested and washed twice in magnesium/calcium free PBS containing 2 mM EDTA. The cells were resuspended in TBS-glucose (24 mM Tris pH7.3, 137 mM NaCl, 2.7 mM KCl, 2 mM glucose) at a concentration of $5 \times 10^5$ cells/ml. Antibody blocking experiments were included in the assay to demonstrate that any observed adhesion is mediated through the integrin VLA4. 10 µg of anti-VLA4 monoclonal antibody (AMAC, USA) was incubated on ice for 30 minutes with 1 ml ($5 \times 10^4$) [$^{14}$C]-labelled Ramos cells. The labelled cells were added at a concentration of approximately $5 \times 10^4$ cells per well with or without 2.5 mM magnesium chloride and antibody. The scintillation microtitre plate was incubated for 30 minutes at 37° C. in a humidified incubator with a 95% air/5% $CO_2$ atmosphere. Following incubation the plate was sealed and unbound cells were removed by inverting the plate several times. The plate was counted on a Wallac Microbeta Scintillation Counter.

Results

Figure 7:
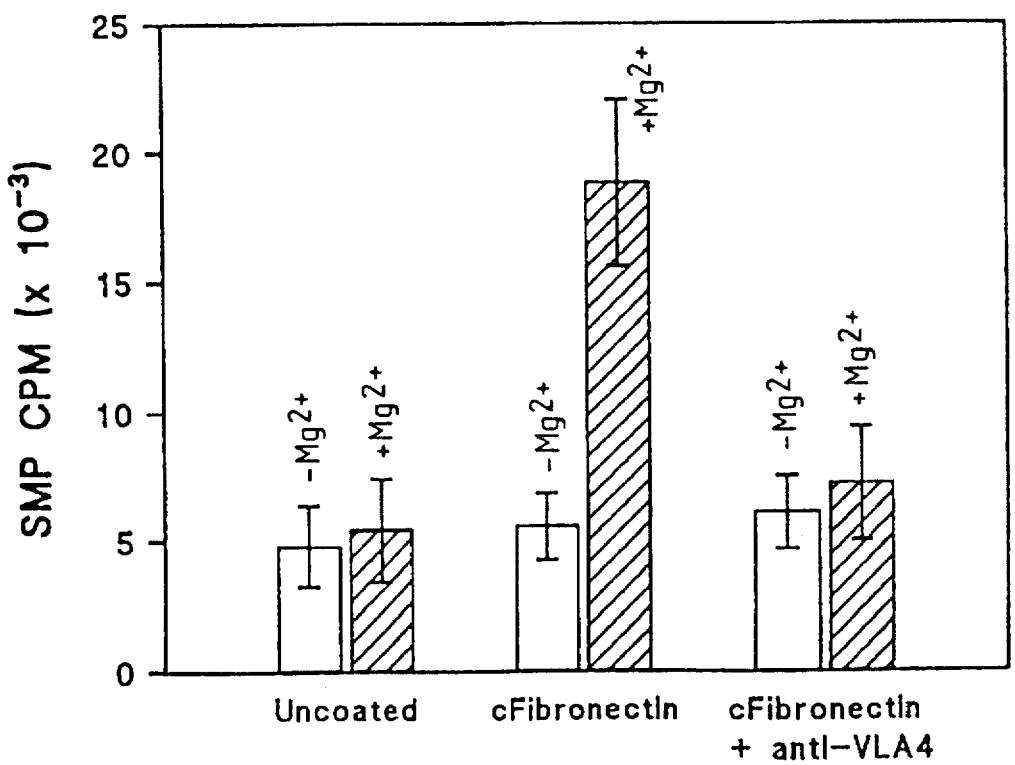

The effect of magnesium ions on VLA4 mediated adhesion of Ramos cells to fibronectin coated scintillation microtitre plates is shown in FIG. 7. Dataset 1 shows the adhesion of control (no $Mg^{++}$ activation) and $Mg^{++}$ activated Ramos cells to uncoated wells. Dataset 2 shows the adhesion of control and activated Ramos cells to wells coated with cellular Fibronectin. Dataset 3 shows the effect of anti-VLA4 monoclonal antibody on the adhesion of control and activated Ramos cells to immobilized fibronectin.

The results show that uncoated wells cannot support $Mg^{++}$ activation dependent adhesion of Ramos cells. The signal obtained represents non specific binding of the cells to the plastic. In fibronectin coated wells, $Mg^{++}$ ion activation results in a 4 fold enhancement of adhesion compared to non specific binding levels. This signal represents the binding of 100% of the Ramos cells to the well surface. The anti-VLA4 monoclonal antibody efficiently blocks the adhesion of $Mg^{++}$ activated cells clearly indicating that adhesion is mediated by the integrin VLA4.

Conclusion

The data in this example indicates that the scintillation microtitre plate can be used to measure activation dependent adhesion of whole cells to soluble counter-ligands immobilized on the surface of the well. Furthermore this example demonstrates the potential for the attachment of unlabelled non-adherent cells in close proximity to the scintillating base plate to enable real time uptake, efflux and binding studies using radiolabelled molecules.

EXAMPLE 5

Measurement of 2 Deoxy-D-[U-$^{14}$C]-Glucose Metabolism in HaCaT Cells

Introduction

The glucose transport process in mammalian cells is mediated by a number of structurally related transporter proteins. With the exception of the kidney and intestinal brush border glucose transporter, all these proteins operate by facilitated diffusion without expense of metabolic energy. However, subsequent metabolism of glucose is often closely coupled to the transport process and occurs rapidly after uptake into the cell. [Clancy, B. M. et. al. (1991). J. Biol. Chem. 266/16 10,122–10,130]

The study of glucose transport has been greatly facilitated by the use of non- or partially metabolized glucose analogues. For example, 3-O-methyl-D-glucose has been extensively used for kinetic studies as this analogue is non-metabolized and can thus enter and leave the cell via the transporter protein without the interference of metabolic processes. This sugar therefore accumulates until equilibrium is reached with the extracellular melieu. [Clancy, B. M. & Czech, M. P. (1990) J. Biol. Chem. 265/21 12,434–12,443]. A useful analogue for investigating steady state uptake rates is 2-deoxy-D-glucose. This sugar is phosphorylated at the C-6 position by hexokinase/glucokinase, but is not further metabolised. The sugar thus becomes trapped within the cell and accumulates at a steady state rate equivalent to the transport and phosphorylation rates, assuming a constant supply of metabolic energy.

In this example we have measured the phosphorylation of 2-deoxy-D-glucose by hexokinase directly using the Scintillation Microtitre Plate and measuring the accumulation of [$^{14}$C]-2-deoxy-D-glucose in the HaCaT keratinocyte cell line.

Materials and Methods

Cell Culture

HaCaT cells (Boukamp, P. et. al., J. Cell. Biol., 106, 761–771 (1988)), a spontaneously immortalized human skin keratinocyte cell line, were cultured in Dulbecco's modification of Eagle's media (DMEM), 2 mM L-glutamine, 50 IU/ml penicillin, 50 µg/ml streptomycin (all from Flow Labs) and 10% foetal calf serum (Advanced Protein Products Ltd) at 37° C. in a humidified incubator with a 95% air/5% $CO_2$ atmosphere.

Uptake of [$^{14}$C] labelled D-glucose and D-glucose analogues

HaCaT cells were seeded at approximately $1 \times 10^5$ cells per well in total DMEM into a 96 well Scintillation Microtitre Plate. The cells were cultured at 37° C. in a humidified atmosphere of 5% $CO_2$ in air for 24 hours. Following incubation, the DMEM was removed and the cells washed twice with phosphate buffered saline solution (PBS—Flow Labs). The cells were left to incubate in 100 µl PBS at room temperature for 1 hour. Following incubation, 10 µl of either 2-Deoxy-D-[U-$^{14}$C]-Glucose (Amersham CFB.181), 3-0-methyl-D-[U-$^{14}$C]-Glucose (Amersham; CFB.141) or D-[U-$^{14}$C]-Glucose (Amersham; CFB.96) was added to the cells at a concentration of 50 µCi/ml.

The uptake of [$^{14}$C] was monitored by direct counting of the plate continuously in the Wallac MicroBeta scintillation counter.

Results

Figure 8:
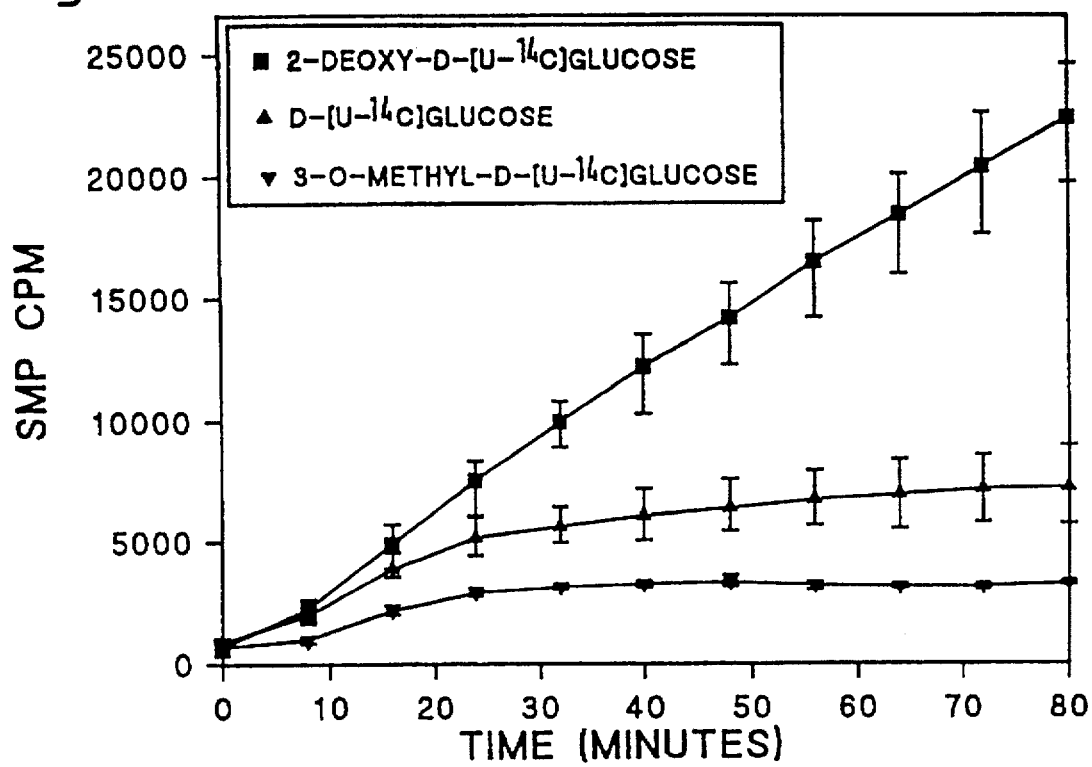

The timecourse for 2-deoxy-D-[U-$^{14}$C]-Glucose uptake and metabolism in HaCaT cells is shown in FIG. 8 (solid squares). Also shown are control uptake profiles for D-[U-$^{14}$C]-Glucose (solid triangles) and 3-O-methyl-D-[U-$^{14}$C]-Glucose (solid inverted triangles). All data points are the mean (± standard deviation) of triplicate wells counted repeatedly during the timecourse.

The non metabolized analogue, 3-O-methyl-D-glucose, accumulates with a profile consistent with the approach to equilibrium between influx and efflux rates. Equilibrium is reached after about 30 minutes incubation at room temperature. D-glucose, which is transported then rapidly metabolized as an energy source, accumulates to a higher level compared to 3-O-methyl-D-glucose. Again the uptake profile tends towards equilibration, this time between the D-glucose influx rate and the efflux of D-glucose and metabolites such as $CO_2$.

The partially metabolized analogue 2-Deoxy-D-glucose shows a different uptake profile with signal accumulating at a linear rate over the period of the timecourse. This represents the accumulation of the specific metabolite 6-phospho-2-deoxy-D-glucose, the product of enzymic phosphorylation by Hexokinase or glucokinase. This phosphorylated derivative cannot be further metabolized nor can it leave the cell and thus accumulates at a rate equivalent to the uptake and phosphorylation process.

Conclusion

This example demonstrates that the Scintillation Microtitre Plate can be used to measure the accumulation of the product of hexokinase or glucokinase by utilizing the analogue 2-deoxy-D-glucose, which can be phosphorylated but not further metabolized. This system can therefore be used for convenient real time analysis of both Hexose transport and subsequent metabolism.

EXAMPLE 6

Measurement of the Hormonal Regulation of [$^{14}$C]-Hexose Transport in the Adipocyte Cell Line 3T3-L1

Introduction

D-Glucose is a major metabolic substrate for many vertebrate tissues. In mammalian systems, the sugar is normally maintained at a fairly constant concentration in the blood by complex homeostatic mechanisms. One of the most important regulators of glucose homeostasis is insulin which rapidly stimulates glucose transport in many cells but particularly in fat and muscle cells. Insulin works primarily by rapidly increasing the number of transporters in the plasma membrane in response to sugar ingestion [Czech, M. P. et. al., (1992), T.I.B.S., 17, 197–200].

A well studied model system for investigating insulin responsive hexose transport is the cultured mouse 3T3 L1 fibroblast. Under appropriate culture conditions, these cells can be induced to differentiate from a fibroblast to an adipocyte phenotype. As adipocytes, these cells show insulin induced enhancement of glucose transport. [Czeck M. P. et. al., (1992) T.I.B.S., 17, 197–200].

We have used this model system, in conjunction with Scintillation Microtitre plates and the partially metabolised glucose analogue 2-deoxy-D-glucose to investigate the potential for real time analysis of hormonal regulation of glucose transport.

Materials and Methods

Cell Culture

3T3-L1 cells (Green, H. et. al., (1974) Cell, 1, 113) a continuous substrain of 3T3 (Swiss albino) which undergo a preadipose to adipose-like conversion, as they progress from rapidly dividing to a confluent and contact inhibited state, were cultured in Dulbecco's modification of Eagle's medium (DMEM), 2 mM L-glutamine, 50 IU/ml penicillin, 50 µg/ml streptomycin (all from Flow Labs) and 10% foetal calf serum (Advanced Protein Products Ltd) at 37° C. in a humidified incubator with a 95% air/5% $CO_2$ atmosphere.

3T3-L1 cells were seeded at approximately 1×10$^5$ cells per well into a 96 well scintillation microtitre plate. The cells were cultured at 37° C. in a humidified atmosphere of 5% $CO_2$ in air for 4 days with a change of media after 2 days. Differentiation was then induced by removing the DMEM and replacing with DMEM also containing 5 µg/ml of insulin (Sigma I1882), 0.25 µM dexamethasone (Sigma D2915) and 0.5 mM 3-isobutyl-1-methylxanthine (Sigma I5879). After 3 days media was removed and replaced with the same media without dexamethasone and 3-isobutyl-1-methylxanthine. Cells were incubated for an additional 3 days after which the media was removed and replaced with DMEM containing 10% foetal calf serum, 2 mM L-glutamine and antibiotics. Differentiation could be visualized microscopically as differentiated cells were characterized by the presence of large fat globules within the cell.

[$^{14}$C] labelled glucose analogue uptake

Nine days after the induction of differentiation the media was removed and the cells washed twice with phosphate buffered saline solution containing magnesium and calcium (PBS-Flow Labs). The cells were then left to incubate in 100 µl PBS at room temperature for 1 hour prior to the addition of [$^{14}$C]. To those cells to be stimulated with insulin, a 10 µl aliquot of insulin was added, to give a 30 nM concentration, 15 minutes prior to adding the [$^{14}$C]. Following PBS incubation, 10 µl of either 2-Deoxy-D[U-$^{14}$C]Glucose (Amersham; CFB181) or 3-O-methyl-D-[U-$^{14}$C]Glucose (Amersham; CFB141) was added to the cells at a concentration of 200 µCi/ml.

The uptake of [$^{14}$C] was monitored by direct counting of the plate continuously in the Packard TopCount scintillation counter.

Results

Figure 9:
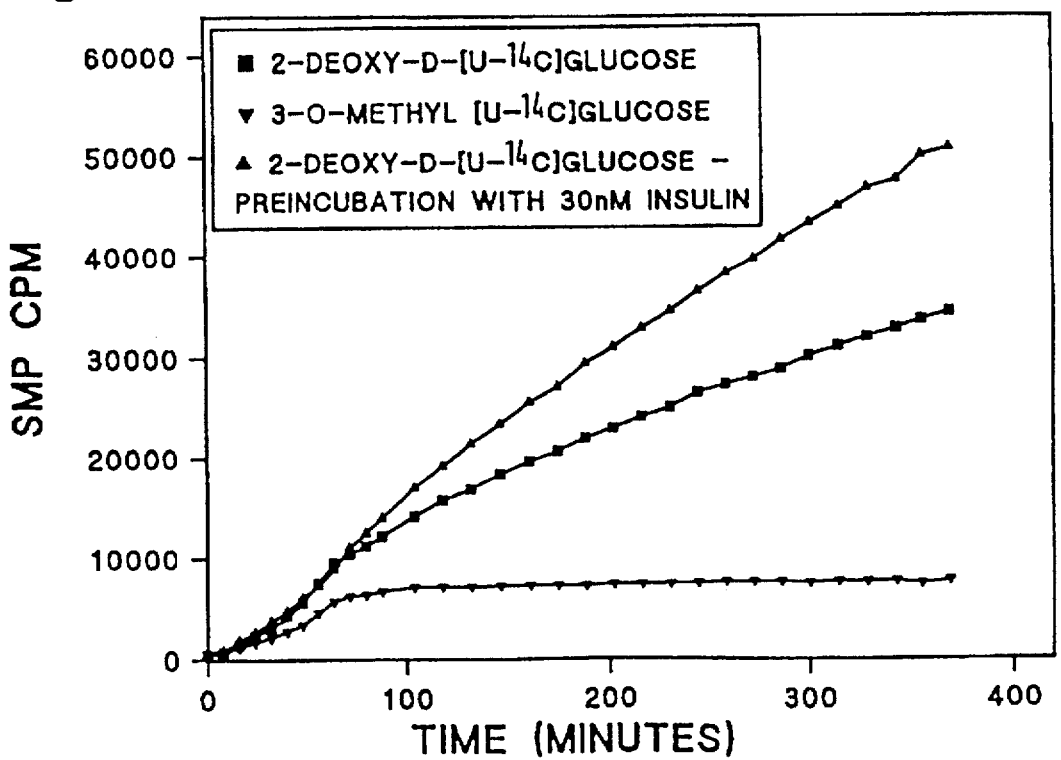

The timecourse for the effect of insulin on 2-deoxy-D-[U-$^{14}$C]-glucose uptake is shown in FIG. 9. Solid squares represent the uptake of control 2-deoxy-D-glucose. Solid triangles show 2-deoxy-D-glucose uptake following preincubation of the differentiated 3T3-L1 cells with 30 nM insulin. Also included as a control is the uptake of the non-metabolized glucose analogue 3-O-methyl-D-glucose.

3-O-methyl glucose is taken into the adipocytes until at equilibrium with the extracellular medium. There is no accumulation of this analogue above the extracellular concentration as the sugar enters by passive facilitated diffusion and is not metabolized in any way. By contrast, 2-deoxy-D-glucose accumulates within the cell over the period of the timecourse as the sugar becomes phosphorylated by hexokinase/glucokinase and trapped within the cells at a rate dependent on the uptake rate. Preincubation of the adipocytes with insulin enhances the rate of accumulation of metabolized 2-deoxy-D-glucose. After 375 minutes incubation, insulin treated cells accumulate approximately 70% more metabolized 2-deoxy-D-glucose compared to control cells. This indicates that hexose uptake in 3T3-L1 adipocytes is regulated in an appropriate way by the exposure of the cells to the hormone insulin.

Conclusion

This example indicates that the Scintillation Microtitre Plate is suitable for the long term growth of cells which can be induced to differentiate into a defined cell type and used in relevant biochemical studies. In this example the invention has successfully been used to measure the hormonal regulation of glucose transport by quantifying the changes in the timecourse for the uptake of 2-deoxy-D-glucose.

EXAMPLE 7

Measurement of Growth Factor Regulation of [Methyl-$^{14}$C]-Thymidine Incorporation in HaCaT Cells Introduction Soluble growth factors have been the subject of intensive research in recent years due to their importance in controlling cellular homeostasis. Defects in growth factor mediated regulatory pathways have been implicated in many disease states and especially in cancer. [Steel, C. M. (1989), Lancet, ii, 30–34].

Two growth factors that have been widely studied with regard to epithelial malignancy are the so called transforming growth factors TGFα and TGFβ. TGFα, which is structurally and functionally related to Epidermal Growth Factor (EGF) and binds to the EGF receptor, mediates a stimulatory growth response. In contrast, TGFβ generally inhibits the proliferation of normal epithelial cells. Overstimulation of the EGF pathway and loss of response to the inhibitory signal mediated by TGFβ are thought to be major factors in the loss of growth control associated with malignancy [Massague, J., (1985), J. Cell Biol., 100, 1508–1514; Gullick, W. J., (1991) Brit. Med. Bull., 47, 87–98].

One of the techniques that is central to the study of cellular response to growth factors is the measurement of DNA synthesis as a marker of cell proliferation. Typically, this involves the quantification of radiolabelled thymidine incorporation into cellular DNA. Most protocols use trichloroacetic acid to precipitate DNA thus necessitating the disruption of the cells. In addition, an extensive and time consuming series of wash and transfer steps are also required. [Hoy, G. A. et. al., (1990) Mol. Cell. Biol., 10/4, 1584–1592]. In this example we have utilized the Scintillation Microtitre Plate to measure growth factor induced modulation of HaCaT cells by noninvasive real time quantification of [methyl-$^{14}$C] thymidine incorporation.

Materials and Methods

Cell Culture

HaCaT cells [Boukamp, P et al, J. Cell. Biol. 106, 761–771 (1988)] a spontaneously immortalized human skin keratinocyte cell line, were cultured in Dulbecco's modification of Eagles Medium with 3.7 g/l sodium bicarbonate (DMEM), 2 mM L-glutamine, 50 IU/ml penicillin, 50 µg/ml streptomycin (all from ICN) and 10% foetal calf serum (Gibco) at 37° C. in a humidified incubator with a 95% air/5% $CO_2$ atmosphere.

[Methyl-$^{14}$C]-thymidine uptake

HaCaT cells were seeded at approx. $1 \times 10^5$ cells per well into a 96-well SMP, in 100 µl DMEM containing 1% foetal calf serum and either 2.0 ng/ml EGF (Sigma E3264) or 0.1 ng/ml TGF-β (Amersham International ARM 30010). Control wells contained no growth factors.

The plate was incubated under the conditions described above for 48 hours (60–80% confluence). Media were then removed and replaced with fresh media and growth factors, containing 0.25 µCi/ml [methyl-$^{14}$C]-thymidine (Amersham International CFA.532, specific activity 56 µCi/mmol), and the plate returned to the incubator. Radiolabelled thymidine uptake was monitored by direct counting of the plate at regular intervals in a Wallac Microbeta Scintillation counter.

Results

Figure 10:
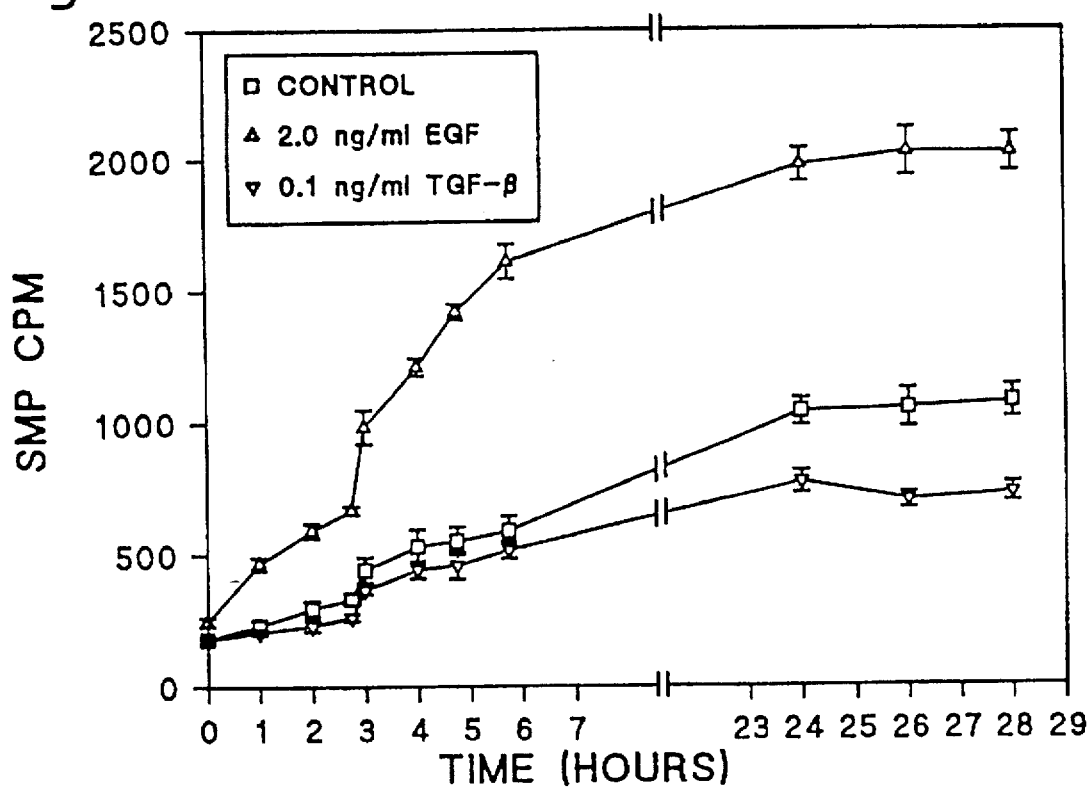

The timecourse showing the effect of EGF and TGFβ on [methyl-$^{14}$C]-thymidine incorporation in HaCaT cells is shown in FIG. 10. Open squares shows the uptake rate in control cells. Open triangles show the thymidine uptake rate in the presence of 2 ng/ml EGF and open inverted triangles show the effect of 0.1 ng/ml TGF-$\beta_1$ on thymidine uptake.

The data indicates that stimulation of HaCaT cells with EGF significantly enhances the uptake of thymidine relative to controls over the first 7 hours of incubation. Exposure of cells to TGF-$\beta_1$ inhibits cell proliferation as shown by a reduced thymidine uptake rate.

The inhibitory effect of TGF-$\beta_1$ is minimal in this system due to the low growth rate of HaCaT cells in 1% serum. These responses are consistent with previously reported effects of these growth factors on HaCaT cell proliferation [Game, S. M. et. al. (1992), Int. J. Cancer, 52, 461–470].

Conclusion

This example indicates that the Scintillation Microtitre Plate can be used to measure cell proliferation by noninvasive quantification of thymidine incorporation into DNA. The assay system can be successfully used to quantify the growth stimulatory and inhibitory effects of soluble growth modulators such as EGF and TGF-$\beta_1$.

Example 8

Measurement of [Methyl-$^3$H]-Thymidine Transport Aphidicolin Treated BHK-21 Fibroblast Cells Introduction The incorporation of radiolabelled thymidine into DNA is a widely used procedure for quantifying cell proliferation. Most protocols measure the incorporation of a pulse of exogeneous thymidine tracer into the acid insoluble cell fraction following the treatment of cells with agents such as trifluoroacetic or perchloric acid [Naito, K. et. al., (1987) Cell Tissue Kinet., 20, 447–457].

There are a number of factors that can influence the uptake of exogeneous thymidine including the position of cells within the cell cycle and the size of the intracellular thymidine pool [Adams, R. L. P. et. al., (1971), Biochim. Biophys. Acta., 240, 455]. It has been reported that the pool size is low at the $G_1/S$ interphase of the cell cycle, but increases significantly during S phase. [Ericksson, S., et al, (1984). Exp. Cell. Res., 155, 129]. These parameters are, therefore, important factors to consider when measuring thymidine uptake rates.

The mycotoxin aphidicolin is a potent inhibitor of nuclear DNA polymerase α and exposure of cells to this agent efficiently blocks DNA synthesis [Spidari, S. et. al., (1982), TIBS., January 1982, 29–32]. In the presence of aphidicolin the thymidine transport process, which is mediated by facilitated diffusion, can be studied in isolation from DNA synthesis. Accurate measurement of thymidine transport can be difficult due to the tendency of thymidine to efflux during the wash steps. A homogeneous assay system, such as the Scintillating Microtitre plate, can potentially overcome this problem by avoiding any washing procedures.

In this example we have used the Scintillation Microtitre Plate to measure [methyl-$^3$H]-thymidine transport in aphidicolin treated BHK-21 fibroblasts synchronised at the $G_1/S$ interphase of the cell cycle.

Materials and Methods

Cell Culture

BHK-21 cells, a hamster kidney fibroblast cell line, were cultured in Dulbecco's modification of Eagle's media with 2 mM L-glutamine 50 IU/ml penicillin 50 µg/ml streptomycin (all from Flow Labs) and 10% foetal calf serum (Advanced Protein Products Ltd) at 37° C. in a humidified incubator with a 95% air/5% $CO_2$ atmosphere. [methyl-$^3$H] Thymidine Transport BHK cells were seeded in 100 µl DMEM at approximately $1 \times 10^5$ cells per well into a 96-well scintillation microtitre plate. The DMEM media was supplemented with 2 µM aminopterin (Sigma; A3411), 200 µM adenosine (Sigma; 4036) and 100 µM glycine (Sigma; 96388) to achieve a synchronous cell population. The cells were cultured at 37° C. in a humidified atmosphere of 5% $CO_2$ in air for 18 hours. Following incubation, 10 µl of 200 µCi/ml [$^3$H]Thymidine (Amersham; TRK 120), 20 µM deoxycytidene (Sigma; D0776) was added to initiate cell proliferation. DNA synthesis was inhibited in the presence of 5 µg/ml aphidicolin (Sigma; A0781).

The Scintillation Microtitre Plates were monitored for [$^3$H]Thymidine Uptake by direct counting of the plate continuously in the Wallac MicroBeta scintillation counter.

Results

Figure 11:
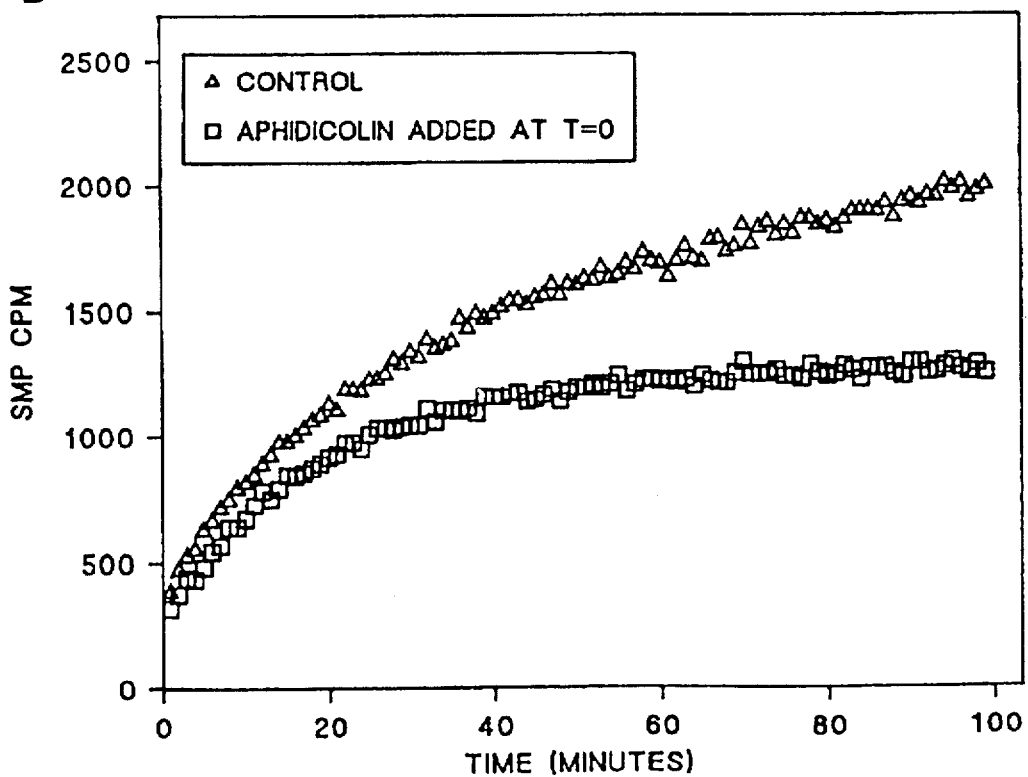

The thymidine transport timecourse for BHK-21 cells is shown in FIG. 11. Open squares represent the transport rate in aphidicolin treated BHK-21 cells. Open triangles show the combined transport and DNA incorporation rates in control cells not inhibited by aphidicolin.

In aphidicolin treated cells, the transport rate follows a profile typical for facilitated diffusion with equilibrium of intracellular and extracellular [$^3$H]-thymidine concentrations reached after approximately 40 minutes incubation at room temperature. Once equilibrium has been reached, the level of incorporated activity remains constant. This is consistent to reported thymidine uptake profiles in the acid soluble fraction of Ehrlich ascites tumour cells [Naito, K., et al, (1987), Cell Tissue Kinet., 20, 447–457].

In the absence of aphidicolin the uptake rate reflects a combination of a linear DNA incorporation rate and a curvilinear thymidine transport profile. From 60 minutes incubation onwards, the observed rate becomes linear as the transport rate reaches equilibrium and does not contribute further to the accumulation of activity.

Conclusion

In this example, the Scintillation Microtitre Plate is shown to be capable of quantifying a rapid transport process simply by direct measurement of the intracellular thymidine concentration. Not only does this greatly facilitate transport and intracellular pool measurements, it enables the simple differentiation between the transport process and the incorporation of thymidine into DNA.

EXAMPLE 9

Measurement of EGF-Induced Motility of [$^{35}$S]-Methionine Labelled 3T3 Cells into Collagen Gels Introduction Cell motility is an important component of many physiological and pathological processes including inflammation, tissue repair, embryogenesis and tumour cell metastasis, and can be controlled by a variety of agents such as growth factors [Rosen, E. M. and Goldberg, I. D., (1993), In Vitro Cell. Dev. Biol. 25: 1079–108], components of the extracellular matrix [Lester, B. R. et. al., (1992), Cancer Metastasis Rev., 11: 31–44)], and tumour-secreted factors [Atnip, K. D. et. al., (1987)., Biochem. Biophys. Res. Comm. 146: 996–1002]. In addition, differences in motility in collagen gels have been observed between different cell lines and cell types, foetal or transformed cells exhibiting greater motility than normal adult cell lines at low serum concentrations [Schor, S. L. et. al., (1985), J. Cell Sci. 73: 235–244].

Traditional methods of measuring cell motility rely on direct counting of stained cells within collagen gels using a light microscope, or on the use of the Boyden Chamber in which cells migrate through a filter immobilised between two layers of medium. At the end of the assay the filter is removed, and cells which have penetrated the filter are fixed, stained and counted to give a single measurement at a given time point.

We have utilized the Scintillation Microtitre plate to show that cell motility into collagen gels can be conveniently measured in real time without disruption of cells.

Materials and Methods

Cell Culture

3T3 mouse embryo fibroblasts (ECACC no. 88031146) were cultured in Dulbecco's modification of Eagle's medium with 3.7 g/l sodium bicarbonate (DMEM), 2 mM L-glutamine, 50 IU/ml penicillin, 50 µg/ml streptomycin (all from ICN) and 10% foetal calf serum (Gibco) at 37° C. in a humidified incubator with a 95% air/5% $CO_2$ atmosphere.

Cell Labelling

Cells were grown in a 75 cm$^2$ cell culture flask until approximately 80% confluent. The medium was then removed and replaced with 20 ml DMEM without methionine (ICN) containing 5 µCi/ml L-[$^{35}$S]-methionine (Amersham International SJ1015, specific activity 10 mCi/ml), and the cells incubated overnight.

Following incubation, the labelling medium was removed and the cells washed twice in 20 ml PBS, trypsinised and resuspended in complete DMEM without phenol red, containing 1% foetal calf serum, and L-glutamine, penicillin, streptomycin as above.

Collagen Gels.

Gels were prepared by rapidly mixing 8.5 ml 2.5 mg/ml Type I collagen from rat's tails (Sigma) with the following on ice:—1 ml sterile-filtered 10x MEM without phenol red (Sigma) containing 20 mM L-glutamine, 500 IU/ml penicillin, 500 µg streptomycin and 10% foetal calf serum; 0.5 ml sodium bicarbonate 4.4% (sterile filtered); 260 µl 2 M NaOH.

The gel mixture (250 µl/well) was pipetted into each well of a sterile non-tissue-culture-treated 96-well scintillation microtitre plate, and allowed to set for 1½ hours at room temperature. The gels were incubated at 37° C. in a 95% air/5% $CO_2$ atmosphere for 1 hour prior to seeding cells.

Cell Motility

Labelled cells were seeded onto collagen gels at a density of 10$^5$ cells/well in 100 µl complete DMEM without phenol red, containing 1% foetal calf serum, with or without 100 ng/ml EGF (equivalent to 28.5 ng/ml in the well) and with L-glutamine, penicillin and streptomycin as described in "cell culture".

The plate was incubated and counted daily for 26 days in the Wallac Microbeta scintillation counter. The medium was replaced every 2–3 days with 100 µl complete DMEM (1% FCS) containing fresh EGF where appropriate. Gels were inspected daily for visible signs of cell motility.

Results

Figure 12:
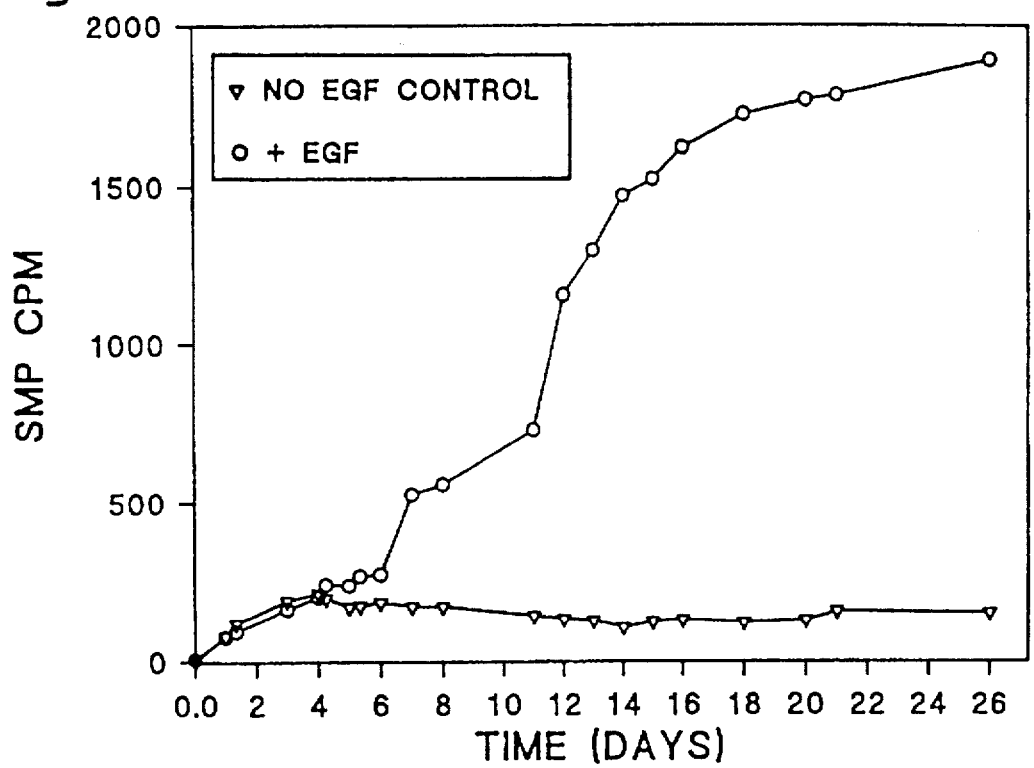

The effect of EGF on 3T3 cell motility within collagen gels is shown in FIG. 12. Open circles represent [$^{35}$S]-methionine labelled 3T3 cells treated with EGF. Open inverted triangles show the signal obtained with untreated control 3T3 cells.

Over the first four days of incubation no difference in detected signal is apparent in control and treated cells. The observed increase in signal during this phase represents [$^{35}$S]-labelled metabolites released by the cells which equilibrate throughout the gel and elicit a non-proximity effect. At this stage, microscopic examination of the gels indicated that no significant motility of the 3T3 cells had occurred.

After 4 days incubation, the EGF treated cells show an approximately linear increase in signal for 12 days after which the signal begins to plateau. During this time, untreated control cells show no increase in signal. Microscopic examination of the collagen gels indicated that EGF treatment induces the cells to migrate into the gel, a small proportion of which reach the scintillating base plate. No significant migration was apparent in untreated controls.

Conclusion

This example indicates that the Scintillation Microtitre Plate can greatly facilitate the quantification of EGF mediated cell motility by detecting the movement of [$^{35}$S]-labelled 3T3 fibroblasts through the collagen gel to the scintillating base-plate. This clearly demonstrates the potential of this invention for real time studies on motility and chemotaxis or any other assay involving the movement of living cells through a matrix.

EXAMPLE 10

Monitoring Zinc Stimulated Incorporation of L[$^{35}$S] Cysteine into BHK-21 Cells Introduction Cells respond to sub-optimal physiological conditions by the activation of stress gene expression and the synthesis of different groups of highly conserved polypeptides.

Exposure to heavy metals induces the expression of metallothioneins, low molecular weight, heavy metal binding proteins rich in cysteine residues. Zinc exposure of both fish [Misra, S. et. al., Biochim. Biophys. Acta, 1007, 325–333, 1989] and mammalian [Hatayama. T. et. al., Mol. Cell. Biochem, 112, 143–153, 1992] cell lines results in mixed responses and the synthesis of both heat shock proteins and metallothioneins.

The Scintillation microtitre Plate was used to demonstrate the real-time stimulation of the uptake and incorporation of L-[$^{35}$S]Cysteine into cellular protein as a stress response to the exposure of cells to zinc. The cells remained intact throughout the monitoring and may subsequently be analysed by standard biochemical techniques such as SDS PAGE.
Materials and Methods
Cell Culture BHK-21 cells derived from the kidneys of oneday old hamsters [Virology, 16, p.147, 1962] were cultured and maintained in Glasgow's modification of Eagles Medium (GMEM) with 2.7 g/l sodium bicarbonate, 2 mM glutamine, 10% foetal calf serum, 10% tryptose, 50 IU penicillin, 50 µg/ml streptomycin, 50 µg/ml Kanamycin (all from Flow Laboratories) at 37° C. in a humidified incubator with 5% $CO_2$ atmosphere.
L-[$^{35}$S]Cysteine uptake Trypsinised and released BHK-21 cells were seeded in GMEM at approximately $1\times10^5$ cells/ml in 100 µl aliquots in a 96-well Scintillation Microtitre plate and incubated for 18 hours in humidified atmosphere of 5% $CO_2$ in air at 37° C. After 18 hours the cells were adapted to Minimum Essential Eagle (Modified) (EMEM) without cysteine, 2.0 g/litre sodium bicarbonate, 2 mM glutamine, 10% foetal calf serum, 50 IU penicillin, 50 µg/ml streptomycin, 50 µg/ml Kanamycin (Flow Laboratores) for 1 hour. This medium was then removed and replaced with the same medium with the addition of 1.0 µCi/ml L-[$^{35}$S]Cysteine, Amersham SJ 232, and where appropriate Zinc, as zinc chloride 1 mM in 5 mM HCl, to give final zinc concentrations of 50, 100 and 150 µM $Zn^{++}$ in the wells.

Figure 13:
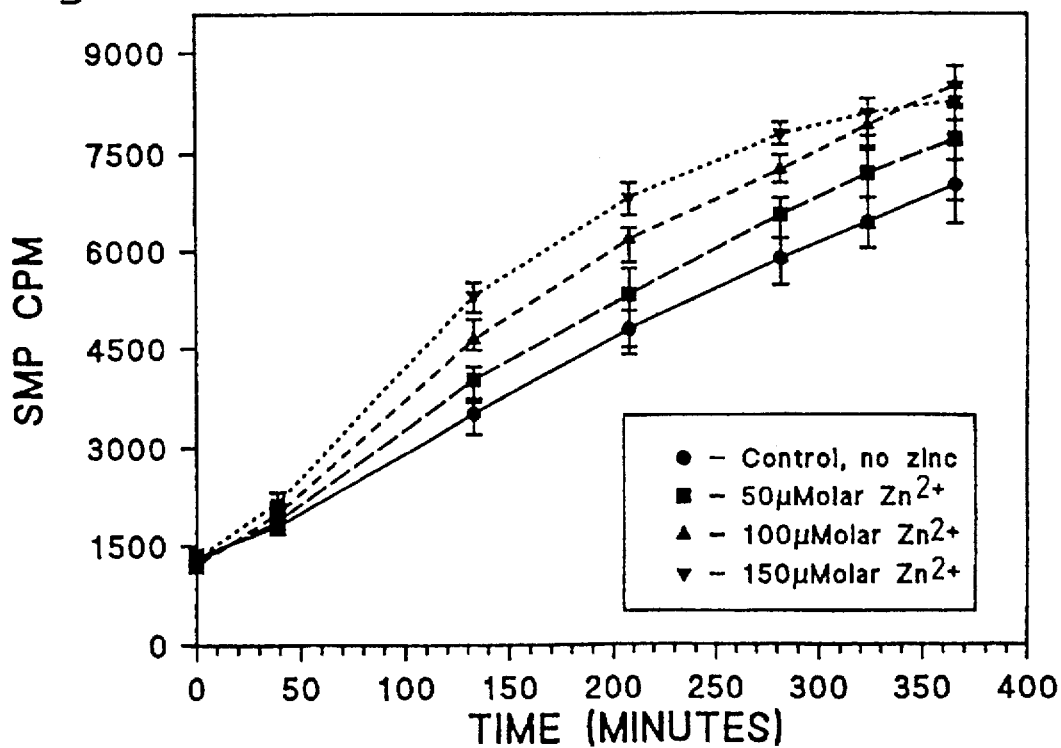

The Scintillation Microtitre plate was then incubated under the conditions previously described for 6 hours and the uptake of the L-[$^{35}$S]Cysteine monitored by direct counting of the plates at convenient intervals using the Wallac 1450 MicroBeta Scintillation counter.
Results A timecourse of L-[$^{35}$S]Cysteine incorporation by BHK-21 cells at increasing concentrations of zinc together with a no zinc control is shown in FIG. 13.

The data illustrates the stimulation of L[$^{35}$S]Cysteine incorporation into BHK-21 cells by zinc and the apparent dose dependency of the cells response to the text increaisng zinc concentration. After 6 hours and at higher zinc concentrations (150 µM) the stimulatory effect declines as the higher zinc concentrations overcome the cells stress responses.

Conclusions

The results illustrate the facility afforded by the Scintillation Microtire Plate in measuring and monitoring the stress response of cells by means of uptake and incorporation of L-[$^{35}$S]Cysteine into cellular proteins. The measurement is achieved without sampling or intervention and uses modest quantities of radioactivity. The cells may be conveniently released from the plate during or after measurement and the specific response or other related responses confirmed by traditional biochemical processes/methods.

EXAMPLE 11

Range of Isotopes used in Device to Monitor Cellular Processes

Introduction

The range of β-particle will travel through an aqueous environment is dependent upon its energy. [Berger & Seltzer (1964), NASA SP, 3012]. The process used in this device relies upon the radiolabel on or within the cells being detectable whilst the radiolabel in free medium remains too far away to allow transfer of the β particle energy and therefore goes undetected. The efficiency and effectiveness of the process described will therefore be limited by the energy of the β-particles or electrons emitted by the radiolabel under study.

We have therefore investigated a series of isotopes emitting β particles up to 1.709 MeV and a range of isotopes with more complex decay patterns for their usefulness in the device.
Materials and Methods
Cell Culture BHK-21 (hamster kidney fibroblasts) and HaCaT (human skin keratinocytes) cells were cultured in Dulbecco's modification of Eagle's Media with 3.7 g/l sodium bicarbonate (DMEM), 2 mM L-glutamine, 50 IU/ml penicillin, 50 µg/ml streptomycin and 10% foetal calf serum (total DMEM) at 37° C. in a humidified incubator with a 95% air/5% $CO_2$ atmosphere.
Isotope Uptake HaCaT cells or BHK-21 cells were seeded at approximately $5\times10^4$ cells/well into 96-well Scintillating Microtitre Plates. The cells were incubated at 37° C. in humidified 95% air/5% $CO_2$ for between 3 and 48 hours. The cells were then either pulsed directly with isotope, or the culture media removed, the adhered cells washed, and DMEM containing the radiolabel added. The final volume within the well ranged from 100–210 µl depending on the assay protocol and isotope used.

The isotopically labelled molecules (all from Amersham International Plc) added to the cells were as follows:

1. L-[methyl-$^3$H]methionine (TRK 853) 82 Ci/mmol, 5 µCi/well.

2. L-[methyl-$^{14}$C]methionine (CFA 152) 55 mCi/mmol, 1 µCi/well.

3. L[$^{35}$S]methionine (SJ 235) 1000 Ci/mmol, 0.9 µCi/well.

4. [$^{33}$P]orthophosphate (BF 1003) 1000 Ci/mmol, 0.6 µCi/well.

5. [$^{32}$P]orthophosphate (PBS 11)>5000 Ci/mmol, 0.5 µCi/well.

6. 5-[$^{125}$I]Iodo-2-deoxyuridine (IM 355) 2000 Ci/mmol, 0.6 µCi/well.

7. Sodium [$^{51}$Cr]chromate (CJS 1P) 25 Ci/mmol, 0.5 µCi/well.

8. [$^{45}$Ca]Calcium chloride (CES 3) 1.8 Ci/mmol, 0.44 μCi/well.

9. [$^{109}$Cd]Cadmium chloride (CUS 1) 100 mCi/mmol, 0.38 μCi/well.

The Scintillating Microtitre Plates were incubated as described above and the uptake of label monitored by direct counting of the plates at regular intervals in a Wallac Microbeta scintillation counter. The observed CPM obtained at T=0 (ie. immediately on addition of label to cells) or CPM obtained with "no cell" control wells were compared to the observed maximal CPM obtained for uptake of radiolabel into cultured cells.

Results

Table 1 shows the observed signal to noise (S/N) ratios for all the different isotopically labelled molecules used in the cellular uptake experiments. Also shown are the maximum emitted energies and the mean path lengths in aqueous medium for each of the isotopes studied. The S/N ratios obtained do not represent the maximum attainable values as experimental and culture conditions varied. However, the results show that, with all the isotopes studied, a S/N ratio of greater than 1 is attained. This indicates that all the molecules and isotopes show some time-dependent accumulation on, or within the cells cultured on the surface of the Scintillation Microtitre Plate.

Conclusion

The data in this example indicates that all isotopes with beta particle/γ ray energies within the range of those tested could be potentially useful in Scintillating Microtitre Plate applications that allow proximate location of the label close to the baseplate. The energy of beta particles from [$^{32}$P] are significantly higher than those of other isotopes tested, however, signal to noise for this isotope still suggests that the use of isotopes with mean particle ranges of 1 or perhaps even 2 mm is not precluded by the results of these studies. The technique would therefore be concluded to be applicable to all radioisotopes with beta particle energies up to 1.709 MeV having a mean path length of up to 1600 μm.

TABLE 1

Signal to noise ratios for the uptake of a range of isotopes into mammalian cells cultured on the scintillation microtitre plate

| Isotope | Max energy of emitted electron (KeV) | Range (μm) mean distance travelled | Signal/noise observed |
|---|---|---|---|
| L-[methyl-$^3$H]methionine | 18 | 1.5[2] | 250 |
| L-[methyl-$^{14}$C]methionine | 155 | 58[2] | 19 |
| L-[$^{35}$S]methionine | 167 | 66[2] | 5 |
| [$^{33}$P]orthophosphate | 249 | 126[2] | 9.5 |
| [$^{45}$Ca]Calcium chloride | 258 | 131[2] | 4.3 |
| [$^{32}$P]orthophosphate | 1709 | 1600[2] | 1.4 |
| 5-[$^{125}$I]Iodo-2-deoxyuridine | 30[3] | 17[5] | 2.4 |
|  | 4[3] | <1[5] |  |
| Sodium [$^{51}$Cr]chromate | 315[4] | 890[5] | 5 |
|  | 5[3] | 1[5] |  |
| [$^{109}$Cd]Cadmium chloride | 84[4] | 104[5] | 25 |
|  | 62[4] | 80[5] |  |

1. Complex mode of decay generating several emitted electrons of different energies.
2. Value is ⅓ max range$^{(see\ ref\ 2)}$ calculated from tables in ref 3).
3. Auger electrons (monoenergetic).
4. Internal conversion electrons (monoenergetic).
5. Values are based on tables in ref 3 and represent maximum range, as well as mean range.

References

1. L'Arnnunziata, M. F., Radionuclide tracers (1987).
2. Spinks, J. W. T. and Woods, R. J., Radiation Chemistry (2nd Edition, 1975)
3. Berger and Seltzer, NASA SP 3012 (1964).

I claim:

1. A multiwell plate comprising an array of wells held in fixed relationship to one another, wherein each well is a vessel having an axis, an open top, opaque side walls and a base, wherein the base includes a region and there is provided in or on an interior surface of the region a layer comprising a scintillant substance and which permits the attachment or growth of cells, and wherein the region of the base and the layer comprising a scintillant substance are both optically transparent.

2. Apparatus as claimed in claim 1, wherein the region of the base is generally perpendicular to the axis of the vessel.

3. Apparatus as claimed in claim 1, wherein the layer comprising a scintillant substance is made of a polymer, in which the monomer units which comprise the polymer include phenyl or naphthyl moieties, the scintillant substance being incorporated in the polymer.

4. Apparatus as claimed in claim 1, wherein the layer has a positively or negatively charged surface.

5. The multiwell plate as claimed in claim 1, wherein the layer comprising a scintillant substance carries a coating selected from the group consisting of charged biopolymers, components of the extracellular matrix, naturally excreted extracellular matrix laid down by cells cultured on the surface, cell adhesion molecules, and cell attachment factors.

6. Apparatus as claimed in claim 1, wherein the layer comprising a scintillant substance constitutes a base plate integral with the base of the vessel.

7. The multiwell plate as claimed in claim 1, comprising a body including side walls of individual wells, and a base plate composed of a polymer comprising the scintillant substance, the base plate sealed to the body so as to constitute closed bottom ends of individual wells.

8. The multiwell plate as claimed in claim 7, wherein said base plate is silk screen printed with a grid array.

9. The multiwell plate as claimed in claim 1, comprising a body including side walls of individual wells, each individual well having a closed bottom end of a polymer comprising the scintillant substance.

10. A method of studying a cellular process, by the use of a multiwell plate comprising an array of wells held in fixed relationship to one another wherein each well is a vessel having an axis, an open top, opaque side walls and base, wherein the base includes a region and there is provided or on an interior surface of the region a layer comprising a scintillant substance and which permits the attachment or growth of cells, and wherein the region of the base and the layer comprising a scintillant substance are both optically transparent, and of detection means for observing scintillation of the scintillant substance, which method comprises providing cells adhering to the layer in the presence of a fluid medium, introducing into the fluid medium a reagent labelled with a radioisotope emitting electrons with a mean range up to 2000 μm in aqueous media, under conditions to cause a portion of the labelled reagent to become associated with or released from the cells adhering to the layer, and using the detection means to observe scintillation caused by radioactive decay so as to study the cellular process.

11. The method as claimed in claim 10, wherein the cells are cultured adhering to the layer within the vessel prior to introduction of the labelled reagent.

12. The method as claimed in claim 10, wherein the cellular process is studied in real time using a non-invasive technique, observation of scintillation being performed in the presence of labelled reagent both associated with the cells and in the fluid medium.

13. The method as claimed in claim 10, wherein the radioisotope is selected from the groups consisting of $^3$H, $^{14}$C, $^{35}$S, $^{33}$P, $^{45}$Ca, $^{32}$P, $^{125}$I, $^{51}$Cr and $^{109}$Cd.

14. The method as claimed in claim 10, wherein the cellular process is selected from the group consisting of biosynthesis, degradation, transport, uptake, movement, adherence, binding, metabolism, infection, fusion, biochemical response, growth and death.

15. A method of studying a cellular process, by the use of a multiwell plate comprising an array of wells held in fixed relationship to one another wherein each well is a vessel having an axis, an open top, opaque side walls and a base, wherein the base includes a region and there is provided in or on an interior surface of the region a layer comprising a scintillant substance and which permits the attachment or growth of cells, and wherein the region of the base and the layer comprising a scintillant substance are both optically transparent, and of detection means for observing scintillation of the scintillant substance, which method comprises introducing into the vessel a fluid suspension of cells labelled with a radioisotope emitting electrons with a mean range of up to 2000 µm in aqueous media, under conditions to cause a portion of the labelled cells to become associated with the layer, or in close proximity to the layer, and using the detection means to observe scintillation caused by radioactive decay so as to study the cellular process.

16. The method as claimed in claim 15, wherein the cellular process is studied in real time using a non-invasive technique, the detection step being performed in the presence of labelled reagent both associated With the cells and in the fluid medium.

17. The method as claimed in claim 15, wherein the radioisotope is selected from the groups consisting of $^3$H, $^{14}$C, $^{35}$S, $^{33}$P, $^{45}$Ca, $^{32}$P, $^{125}$I, $^{51}$Cr and $^{109}$Cd.

18. The method as claimed in claim 15, wherein the cellular process is selected from the groups consisting of biosynthesis, degradation, transport, uptake, movement, adherence, binding, metabolism, infection, fusion, biochemical response, growth and death.

\* \* \* \* \*